US011267787B2

(12) United States Patent
Morikawa et al.

(10) Patent No.: US 11,267,787 B2
(45) Date of Patent: Mar. 8, 2022

(54) METHOD FOR PRODUCING QUINOLIN-4(1H)-ONE DERIVATIVE

(71) Applicants: NIPPON KAYAKU CO., LTD., Tokyo (JP); MEIJI SEIKA PHARMA CO., LTD., Tokyo (JP)

(72) Inventors: Akinori Morikawa, Ibaraki (JP); Hirokazu Kuroda, Ibaraki (JP); Kazumi Yamamoto, Kanagawa (JP); Nozomu Nakanishi, Kanagawa (JP)

(73) Assignees: NIPPON KAYAKU CO., LTD, Tokyo (JP); MEIJI SEIKA PHARMA CO., LTD., Tokyo (JP)

( * ) Notice: Subject to any disclaimer, the term of this patent is extended or adjusted under 35 U.S.C. 154(b) by 0 days.

(21) Appl. No.: 16/771,838

(22) PCT Filed: Dec. 12, 2018

(86) PCT No.: PCT/JP2018/045596

§ 371 (c)(1),
(2) Date: Jun. 11, 2020

(87) PCT Pub. No.: WO2019/117179

PCT Pub. Date: Jun. 20, 2019

(65) Prior Publication Data

US 2021/0070710 A1 Mar. 11, 2021

(30) Foreign Application Priority Data

Dec. 12, 2017 (JP) ............................ JP2017-238004

(51) Int. Cl.
*C07D 215/233* (2006.01)

(52) U.S. Cl.
CPC ................................ *C07D 215/233* (2013.01)

(58) Field of Classification Search
CPC .................................................. C07D 215/233
See application file for complete search history.

(56) References Cited

U.S. PATENT DOCUMENTS

| | | | |
|---|---|---|---|
| 8,367,833 B2 * | 2/2013 | Kato .................... | C07D 215/20 546/159 |
| 2003/0119863 A1 | 6/2003 | Yamamoto et al. | |
| 2003/0144314 A1 | 7/2003 | Doran et al. | |
| 2007/0203181 A1 | 8/2007 | Yamamoto et al. | |
| 2011/0118468 A1 | 5/2011 | Kato et al. | |

FOREIGN PATENT DOCUMENTS

| | | | |
|---|---|---|---|
| EP | 2 305 649 | | 4/2011 |
| JP | 2005/501104 | * | 1/2005 |
| JP | 2005-501104 | | 1/2005 |
| JP | 2007-77156 | | 3/2007 |
| TW | 201014528 | | 4/2010 |
| WO | 2006/013 896 | | 2/2006 |
| WO | 2010/007964 | * | 1/2010 |
| WO | 2011/105349 | | 9/2011 |
| WO | 2012/167237 | | 12/2012 |

OTHER PUBLICATIONS

International Preliminary Report on Patentability dated Jun. 25, 2020 in corresponding International (PCT) Application No. PCT/JP2018/045596.
International Search Report (ISR) dated Mar. 19, 2019 in International (PCT) Application No. PCT/JP2018/045596.
Hikaru Abe et al., "Synthesis of Intervenolin, an Antitumor Natural Quinolone willi Unusual Substituents", Organic Letters, vol. 15, No. 9, pp. 2124-2127, 2013, cited in the specification.
George A. Reynolds et al., "A Publication of ReHable Methods for the Preparation of Organic Compounds, 2-Methyl-4-Hydroxyquinoline", Organic Syntheses, Coli. vol. 3, p. 593, 1955; vol. 29, p. 70, 1949, cited in the specification.
Indian Office Action dated Jul. 30, 2021 in corresponding Indian Patent Application No. 202017024746, with English translation.

* cited by examiner

*Primary Examiner* — D Margaret M Seaman
(74) *Attorney, Agent, or Firm* — Wenderoth, Lind & Ponack, L.L.P.

(57) ABSTRACT

[Problem] The present invention provides a method for producing and isolating a target quinolone derivative using general industrial facilities with high purity.

[Solving means] The present invention also provides a method for producing a quinolone derivative, the method including reacting a ketone with an anthranilic acid derivative using an aluminum halide and removing the aluminum halide under basic conditions.

11 Claims, No Drawings

METHOD FOR PRODUCING QUINOLIN-4(1H)-ONE DERIVATIVE

CROSS-REFERENCE TO RELATED APPLICATION

This application is based upon and claims the benefit of priority from Japanese Patent Application No. 2017-238004, filed on Dec. 12, 2017; the entire contents of which are incorporated herein by reference.

TECHNICAL FIELD

The present invention relates to a method for producing a derivative having a quinolin-4(1H)-one skeleton (hereinafter referred to as quinolone derivative) useful as pharmaceutical and agricultural intermediates.

BACKGROUND ART

In recent days, many quinolone derivatives have been reported as active pharmaceutical and agricultural ingredients and pharmaceutical and agricultural intermediates. It is widely known that quinolone derivatives are used, for example, as synthetic intermediates in the production of quinoline derivatives. Patent Document 1 discloses a quinoline derivative in the pharmaceutical field as an antimalarially active compound, and Non-Patent Document 1 discloses a quinoline derivative as a compound having antitumor activity.

In the agricultural field, Patent Document 2 discloses a quinoline derivative as an agricultural and horticultural insecticide, and Patent Document 3 discloses a quinoline derivative as an agricultural and horticultural fungicide.

In the methods for producing a quinoline derivative disclosed in all the documents, the quinolone derivative is mentioned as an important synthetic intermediate and, according to the methods for producing a quinolone derivative disclosed in Patent Documents 2, 3, Non-Patent Documents 1 and 2, an aniline derivative as a precursor and a β-ketoester or a malonic acid compound under acidic conditions and/or in an aromatic solvent are heated to produce the quinolone derivative. However, these production methods require a reaction at a very high temperature of 200° C. or higher and/or in the presence of a large amount of an acid. Therefore, these production methods are not suitable for the conditions of general industrial facilities. There are also problems with the stability of the aniline derivative as a raw material, and the regioselectivity of a reaction site, thus failing to produce a target quinolone derivative with high yield and high selectivity.

Patent Document 4 discloses, as the method for producing a quinolone derivative mentioned in Patent Document 3, a production method that solved the problem with the regioselectivity of a reaction site in which an anthranilic acid derivative is used in place of an aniline derivative and a ketone is used as a raw material in place of a β-ketoester, and aluminum chloride is used under reflux of xylene. In this production method, a quinolone derivative which is commonly hardly soluble in various solvents is separated from aluminum chloride under hydrochloric acid conditions and is isolated by filtration. However, the material of filtration facilities used industrially is generally a metal, and it is difficult to industrially obtain a target product by the above-mentioned production method due to a problem with corrosiveness. Moreover, in the production method, a ketone, which is a relatively expensive main raw material, is used in a large excess amount of about 4.5-fold mol relative to 1 mol of an anthranilic acid derivative, so that it is hard to say that the production method is an industrially suitable production method. In the above production method, an alcohol solvent is used in a large amount of about 1,000 mL relative to 1 mol of an anthranilic acid derivative during heating and washing in a post-treatment after the reaction, so that the method is industrially and environmentally disadvantageous in view of an increase volume and excessive use of the solvents.

RELATED ART DOCUMENTS

Patent Documents

[Patent Document 1] WO 2012/167237
[Patent Document 2] WO 2006/013896
[Patent Document 3] JP 2007-077156 A
[Patent Document 4] WO 2010/007964

Non-Patent Documents

[Non-Patent Document 1] ORGANIC LETTERS, Vol. 15(9), p. 2124-2127, "Synthesis of Intervenolin, an Antitumor Natural Quinolone with Unusual Substituents"

[Non-Patent Document 2] Organic Syntheses, Vol. 29, p. 70 "2-Methyl-4-hydroxyquinoline"

SUMMARY OF THE INVENTION

An object of the present invention is to provide a method for producing and isolating a target quinolone derivative under general industrial facility requirements with high purity.

As a result of intensive study, the present inventors have fund that, using an aluminum halide represented by genera formula (1), a ketone represented by general formula (2) is reacted with an anthranilic acid derivative represented by general formula (6) and then aluminum chloride is separated under basic conditions, thus making it possible to produce and isolate a target quinolone derivative with high purity under general industrial facility requirements. They have also found that an aluminum halide represented by general formula (1) is mixed in advance with a ketone represented by general formula (2) and, if necessary, the mixture thus obtained is further mixed with a sulfide represented by general formula (4), thus making it possible to produce and isolate a quinolone derivative represented by general formula (7) with high yield and high selectivity using an anthranilic acid derivative represented by general formula (6) as a starting material, and to reduce the raw material. They have also found that by replacing the alcohol to be used with a higher alcohol equally high or higher than ethanol, it is possible to reduce the amount of the alcohol used, According to the present invention, the following inventions are provided.

[1] A method for producing a quinolone derivative represented by general formula (7):

[Chemical Formula 4]

(7)

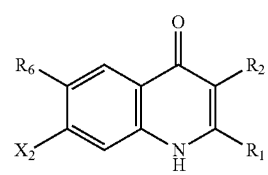

wherein $R_1$, $R_2$, $R_6$, and $X_2$ are as defined below, the method including using an aluminum halide represented by general formula (1):

[Chemical Formula 1]

$$AlZ_3 \quad (1)$$

wherein Z represents a halogen atom, reacting a ketone represented by general formula 2):

[Chemical Formula 2]

(2)

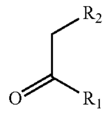

wherein $R_1$, and $R_2$ each independently represent;

an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{3-8}$ cyclic aliphatic hydrocarbon group, an optionally substituted aromatic hydrocarbon group, or an optionally substituted heterocyclic group, alternatively, $R_1$ and $R_2$ are combined together to represent a group —$(CH_2)_p$— (in which p represents 2 to 6), wherein each of the substituents in the linear or branched $C_{1-4}$ alkyl group, the linear or branched $C_{2-4}$ alkenyl group and the linear or branched $C_{2-4}$ alkynyl group is at least one group selected from the group consisting of a halogen atom, and a $C_{1-4}$ alkoxy group optionally substituted with a halogen atom, the substituent in the $C_{3-8}$ cyclic aliphatic hydrocarbon group is at least one group selected from the group consisting of a linear or branched $C_{1-4}$ alkyl group, a halogen atom, and a $C_{1-4}$ alkoxy group optionally substituted with a halogen atom, the substituent in the aromatic hydrocarbon group is at least one group selected from the group consisting of a halogen atom, a linear or branched $C_{1-4}$ alkyl group optionally substituted with a halogen atom, a linear or branched $C_{1-4}$ alkoxy group optionally substituted with a halogen atom, and a phenoxy group which is optionally substituted with a linear or branched $C_{1-4}$ alkoxy group optionally substituted with a halogen atom, and the substituent in the heterocyclic group is at least one group selected from the group consisting of a halogen atom, a linear or branched $C_{1-4}$ alkyl group optionally substituted with a halogen atom, and a linear or branched $C_{1-4}$ alkoxy group optionally substituted with a halogen atom, with an anthranilic acid derivative represented by general formula (6):

[Chemical Formula 3]

(6)

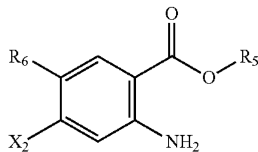

wherein $R_5$ represents:

an optionally substituted linear or branched $C_{1-4}$ alkyl group, or an optionally substituted $C_{3-8}$ cyclic aliphatic hydrocarbon group, $R_6$ represents a hydrogen atom, a halogen atom, or —B—$R_7$, wherein, B represents:

an oxygen atom, a sulfuratom $N(R_8)$, $N(R_8)$—CO or CO—$N(R_8)$, $R_7$ and $R_8$ each independently represent:

a hydrogen atom, an optionally substituted linear or branched $C_{1-4}$ alkyl group, an optionally s substituted linear or branched $C_{2-4}$ alkenyl group, an optionally substituted linear or branched $C_{2-4}$ alkynyl group, an optionally substituted $C_{3-8}$ cyclic aliphatic hydrocarbon group, an optionally substituted aromatic hydrocarbon group, or an optionally substituted heterocyclic group, wherein each of the substituents in the linear or branched $C_{1-4}$ alkyl group, the linear or branched $C_{2-4}$ alkenyl group, and the linear or branched $C_{2-4}$ alkynyl group is at least one group selected from the group consisting of a halogen atom, and a $C_{1-4}$ alkoxy group optionally substituted with a halogen atom, the substituent in the $C_{3-8}$ cyclic aliphatic hydrocarbon group is at least one group selected from the group consisting of a linear or branched $C_{1-4}$ alkyl group, a halogen atom, and a $C_{1-4}$ alkoxy group optionally substituted with a halogen atom, and each of the substituents in the aromatic hydrocarbon group and the heterocyclic group is at least one group selected from the group consisting of:

a halogen atom, a linear or branched $C_{1-4}$ alkyl group optionally substituted with a halogen atom, a linear or branched $C_{1-4}$ alkyl group which is optionally substituted with a $C_{1-4}$ alkoxy group optionally substituted with a halogen atom, a linear or branched $C_{2-4}$ alkenyl group optionally substituted with a halogen atom, a linear or branched $C_{2-4}$ alkenyl group which is optionally substituted with a $C_{1-4}$ alkoxy group optionally substituted with a halogen atom, a linear or branched $C_{2-4}$ alkynyl group optionally substituted with a halogen atom, a linear or branched $C_{2-4}$ alkynyl group which is optionally substituted with a $C_{1-4}$ alkoxy group optionally substituted with a halogen atom, a linear or branched $C_{1-4}$ alkoxy group optionally substituted with a halogen atom, a linear or branched $C_{1-4}$ alkoxy group which is optionally substituted with a $C_{1-4}$ alkoxy group optionally substituted with a halogen atom, a linear or branched $C_{2-4}$ alkenyloxy group optionally substituted with a halogen atom, a linear or branched $C_{2-4}$ alkenyloxy group which is optionally substituted with a $C_{1-4}$ alkoxy group optionally substituted with a halogen atom, a linear or branched $C_{2-4}$ alkynyloxy group optionally substituted with a halogen atom, a linear or branched $C_{2-4}$ alkynyloxy group which is optionally substituted with a $C_{1-4}$ alkoxy group optionally substituted with a halogen atom, and a phenoxy group which is optionally substituted with a linear or branched $C_{1-4}$ alkoxy group optionally substituted with a halogen atom, and $X_2$ represents:

a hydrogen atom, a halogen atom, an optionally substituted linear or branched $C_{1-4}$ alkyl group, or an optionally substituted linear or branched $C_{1-4}$ alkoxy group, in which each of the substituents in the linear or branched $C_{1-4}$ alkyl group, and the linear or branched $C_{1-4}$ alkoxy group is at least one group selected from the group consisting of a halogen atom, and a $C_{1-4}$ alkoxy group optionally substituted with a halogen atom; and removing the aluminum halide under basic conditions,

[2] The method according to [1], including a step of mixing the aluminum halide represented by general formula (1) in advance with the ketone represented by general formula (2).

[3] The method according to [1] or [2], including a step of further adding a sulfide represented by general formula (4):

[Chemical Formula 5]

$$R_3—S(=O)_l—R_4 \quad (4)$$

in which $R_3$ and $R_4$ each independently represent an optionally substituted linear or branched $C_{1-4}$ alkyl group, or $R_3$ and $R_4$ are combined together to represent a group $—(CH_2)_q—$ (q is 3 to 7), and 1 represents 1 or 2, to a mixture of the aluminum halide represented by general formula (1) and the ketone represented by general formula (2).

[4] The method according to [3], wherein

Z represents a halogen atom, $R_1$ and $R_2$ each independently represent:

an optionally substituted linear or branched $C_{1-4}$ alkyl group, an optionally substituted linear or branched $C_{2-4}$ alkenyl group, or an optionally substituted linear or branched $C_{2-4}$ alkynyl group, in which each of the substituents in the linear or branched $C_{1-4}$ alkyl group, the linear or branched $C_{2-4}$ alkenyl group, and the linear or branched $C_{2-4}$ alkynyl group is at least one group selected from the group consisting of a halogen atom, and a $C_{1-4}$ alkoxy group optionally substituted with a halogen atom, $R_3$ and $R_4$ are combined together to represent group $—(CH_2)_q—$ (q is 3 to 7), and l represents 1 or 2, $R_5$ represents a linear or branched $C_{1-4}$ alkyl group, or a $C_{3-8}$ cyclic aliphatic hydrocarbon group, $R_6$ represents a hydrogen atom, a halogen atom, or $—B—R_7$, wherein B represents an oxygen atom, sulfur atom, $N(R_8)$ $N(R_8)—CO$, or $CO—N(R_8)$, $R_7$ and $R_8$ each independently represent a halogen atom, or an aromatic hydrocarbon group which is optionally substituted with a linear or branched $C_{1-4}$ alkoxy group optionally substituted with a halogen atom, and $X_2$ represents a hydrogen atom, a halogen atom, a linear or branched $C_{1-4}$ alkyl group optionally substituted with a halogen atom, or a linear or branched $C_{1-4}$ alkoxy group optionally substituted with a halogen atom.

[5] The method according to any one of [1] to [4], wherein the aluminum halide represented by general formula (1) is aluminum chloride.

[6] The method according to any one of [1] to [5], wherein the ketone represented by general formula (2) is 3-pentanone

[7] The method according to any one of [1] to [6], wherein the anthranilic acid derivative represented by general formula (6) represents the following general formula (8):

[Chemical Formula 6]

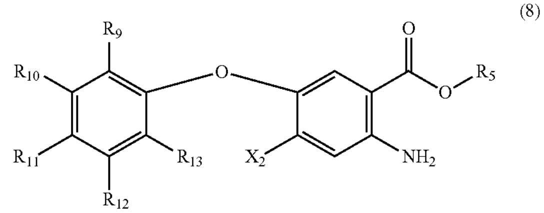

wherein $R_5$ and $X_2$ are as defined above, $R_9$, $R_{10}$, $R_{11}$, $R_{12}$, and $R_{13}$ each independently represent:

a hydrogen atom, a halogen atom, an optionally substituted, linear or branched $C_{1-4}$ alkyl group, an optionally substituted linear or branched $C_{2-4}$ alkenyl group, an optionally substituted linear or branched $C_{2-4}$ alkynyl group, an optionally substituted linear or branched $C_{1-4}$ alkoxy group, an optionally substituted linear or branched $C_{2-4}$ alkenyloxy group, or, an optionally substituted linear or branched $C_{2-4}$ alkynyloxy group, in which each of the substituents in $R_9$, $R_{10}$, $R_{11}$, $R_{12}$, and $R_{13}$ is at least one group selected from the group consisting of a halogen atom, and a $C_{1-4}$ alkoxy group optionally substituted with a halogen atom.

[8] The method according to any one of [1] to [7], wherein the sulfide represented by general formula (4) is tetrahydrothiophene-1,1-dioxide,

[9] The method according to any one of [1] to [8], wherein the removal of the aluminum halide under basic conditions is performed by filtration under basic conditions using an aqueous caustic solution and an alcohol.

[10] The method according to [2], wherein, in the step of mixing the aluminum halide represented by general formula (1) in advance with the ketone represented by general formula (2), an aluminum halide mixture represented by general formula (3):

[Chemical Formula 7]

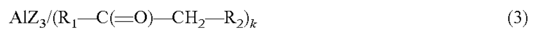

$$AlZ_3/(R_1—C(=O)—CH_2—R_2)_k \quad (3)$$

wherein Z, $R_1$, and $R_2$ are as defined above, and k represents a numeral of 1 or more is prepared.

[11] The method according to [10], including a step of further adding a sulfide represented by general formula (4) to an aluminum halide mixture represented by general formula (3) to prepare an aluminum halide mixture represented by general formula (5):

[Chemical Formula 8]

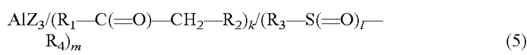

$AlZ_3/(R_1—C(=O)—CH_2—R_2)_k/(R_3—S(=O)_l—R_4)_m$ (5)

wherein Z, $R_1$, $R_2$, $R_3$, $R_4$, k, and l are as defined above, and m represents a numeral of 0 or more.

[12] The method according to any one of [1] to [7], wherein the quinolone derivative represented by general formula (7) represents the following general formula (9):

[Chemical Formula 9]

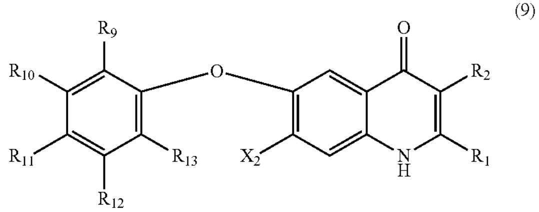

wherein $R_1$, $R_2$, $R_9$, $R_{10}$, $R_{11}$, $R_{12}$, $R_{13}$, and $X_2$ are as defined above.

[13] The method according to any one of [1] to [12], wherein the quinolone derivative represented by general formula (7) to be produced is 2-ethyl-3,7-dimethyl-6-(4-(trifluoromethoxy)phenoxy)quinolin-4 (1H)-one.

Using an aluminum halide represented by general formula (1), a ketone represented by general formula (2) is reacted with an anthranilic acid derivative represented by general formula (6) and then aluminum chloride is separated under basic conditions, thus making it possible to produce and isolate a target quinolone derivative with high purity under general industrial facility requirements. An aluminum halide represented by general formula (1) is mixed in advance with a ketone represented by general formula (2) and, if necessary, a sulfide represented by general formula (4) is further mixed, thus making it possible to produce and isolate a quinolone derivative represented by general formula (7) with high yield and high selectivity. The alcohol to be used is replaced with a higher alcohol equally high or higher than ethanol, thus making it possible to reduce the amount of the alcohol used.

DETAILED DESCRIPTION OF THE INVENTION

In the present invention, quinolin-4(1H)-one (quinolone) has a tautomeric relationship with 4-hydroxyquinoline, and is regarded as a synonymous substance in the present specification.

The definition of substituents or groups in general formulas provides a general definition of a compound according to the present invention. Suitable substituents and/or groups in the general formulas mentioned above and below will be specifically described below.

Z represents a halogen atom. As used herein, “halogen atom” includes fluorine, chlorine, bromine, or iodine, preferably fluorine, chlorine or bromine, and most preferably chlorine.

As used herein, “cyclic aliphatic hydrocarbon group” represents a saturated or unsaturated cyclic aliphatic hydrocarbon group, and examples thereof include cyclic alkyl such as a cycloalkyl group, a cycloalkenyl group, a cycloalkynyl group, a bicycloalkyl group and the like. The number of carbon atoms thereof is not particularly limited and is 3 to 10, preferably 3 to 8, and more preferably 3 to 6.

Specific examples of the cyclic aliphatic hydrocarbon group include a cyclopropyl group, a cyclobutyl group, a cyclopentyl group, a cyclohexyl group, a cyclooctyl group, a cyclopropenyl group, a cyclobutenyl group, a bicycloheptyl group, a bicyclooctyl group, a decanyl group and the like, preferably a cyclopropyl group, a cyclopentyl group, or a cyclohexyl group.

As used herein, regarding “aromatic hydrocarbon group”, the number of carbon atoms thereof is not particularly limited and is 3 to 15, and preferably 6 to 10. The aromatic hydrocarbon group may be a group in which one or more aromatic rings (for example, aromatic rings having 4 to 7 carbon atoms) are bonded (including condensation).

Specific examples of the aromatic hydrocarbon group include a phenyl group, a naphthyl group, an anthracenyl group, a phenanthryl group and the like, preferably a phenyl group or a naphthyl group.

As used herein, “heterocyclic group” includes a 3- to 10-membered cyclic substituent having one, or more cyclic structures optionally having an unsaturated bond, or a 3- to 10-membered aromatic ring having one or more cyclic structures, each containing one or more heteroatoms individually selected from S, O or N, preferably a 5- or 6-membered heterocyclic saturated or aromatic ring containing one S, O or N as a heteroatom, a 5- or 6-membered heterocyclic saturated or aromatic ring containing two N as heteroatoms, or a 5- or 6-membered heterocyclic saturated or aromatic ring containing O or S and one N as heteroatoms.

Specific examples of the heterocyclic group include a thienyl group such as a (2- or 3-)thienyl group, a furyl group such as a (2- or 3-)furyl group, a pyrrolyl group such as a (1-, 2- or 3-)pyrrolyl group, an imidazolyl group such as a (1- or 2-)imidazolyl group, a pyrazolyl group such as a (1-, 3-, 4- or 5-)pyrazolyl group, an isothiazolyl group such as a (3-, 4- or 5-)isothiazolyl group, an isoxazolyl group such as a (3-, 4- or 5-)isoxazolyl group, a thiazolyl group such as a (2-, 4- or 5-)thiazolyl group, an oxazolyl group such as a (2-, 4- or 5-)oxazolyl group, a pyridyl group such as a (2-, 3- or 4-)pyridyl group, or a pyrimidinyl group such as a (2-, 4-, 5- or 6-)pyrimidinyl group, preferably a pyridyl group or a thienyl group.

The linear or branched $C_{1-4}$ alkyl group represented by $R_1$, $R_2$, $R_3$, $R_4$, $R_5$, $R_7$, $R_8$, and $X_2$ may be either linear or branched and represents a $C_{1-4}$ alkyl group, preferably a linear or branched $C_{1-3}$ alkyl group.

Specific examples of the linear or branched $C_{1-4}$ alkyl group represented by $R_1$, $R_2$, $R_3$, $R_4$, $R_5$, $R_7$, $R_8$, and $X_2$ include a methyl group, an ethyl group, a propyl group, an i-propyl group, an n-butyl group, an i-butyl group, a s-butyl group, a t-butyl group, preferably a methyl group, an ethyl group, a propyl group, an i-propyl group, or an n-butyl group, and more, preferably a methyl group, an ethyl group, a propyl group, or an i-propyl group.

The linear or branched $C_{1-4}$ alkyl group represented by $R_1$, $R_2$, $R_3$, $R_4$, $R_5$, $R_7$, $R_8$, and $X_2$ is optionally substituted, and examples of the substituent thereof include at least one group selected from the group consisting of a halogen atom, a linear or branched $C_{1-4}$ alkoxy group, a linear or branched $C_{1-4}$ alkoxy group optionally substituted with a halogen atom, an optionally substituted aromatic hydrocarbon group, and an optionally substituted heterocyclic group, preferably at least one group selected from the group consisting of a halogen atom, and a linear or branched $C_{1-4}$ alkoxy group optionally substituted with a halogen atom. When two or more halogen atoms are present, they may be the same or different. Examples of the substituent of the aromatic hydrocarbon group and the heterocyclic group include at least one group selected from the group consisting of a halogen atom, a linear or branched $C_{1-4}$ alkoxy group optionally substituted with a halogen atom, and an alkoxy group which is optionally substituted with a linear or branched $C_{1-4}$ alkoxy group optionally substituted with a halogen atom, preferably at least one group selected from the group consisting of a halogen atom, and a linear or branched $C_{1-4}$ alkoxy group optionally substituted with a halogen atom.

Specific examples of the optionally substituted linear or branched $C_{1-4}$ alkyl group represented by $R_1$, $R_2$, $R_3$, $R_4$, $R_5$, $R_7$, $R_8$, and $X_2$ include, in addition to specific examples of the above-mentioned unsubstituted linear or branched $C_{1-4}$ alkyl group, a trifluoromethyl group, a pentafluoroethyl group, a heptafluoro-n-propyl group, a heptafluoro-i-propyl group, a chloromethyl group, a trichloromethyl group, a (1- or 2-)chloroethyl group, a 2,2,2-trifluoroethyl group, a 1,1,2,2-tetrafluoroethyl group, a pentafluoroethyl group, a methoxymethyl group, a 2-trifluoromethoxyethyl group, a benzyl group, a (4-(4-(trifluoromethoxy))phenoxy)benzyl group, a pyridylmethyl group and the like, preferably a trifluoromethyl group, a pentafluoroethyl group, a heptafluoro-n-propyl group, a heptafluoro-i-propyl group, a (4-(4-(trifluoromethoxy))phenoxy)benzyl group, or a pyridylmethyl group, and more preferably a trifluoromethyl group, The linear or branched $C_{2-4}$ alkenyl group represented by $R_1$, $R_2$, $R_7$, and $R_8$ may be either linear or branched, and represents a $C_{2-4}$ alkenyl group, preferably a linear or branched $C_{2-3}$ alkenyl group.

Specific examples of the linear or branched $C_{2-4}$ alkenyl group represented by $R_1$, $R_2$, $R_7$, and $R_8$ include a vinyl group, a 1-propenyl group, a 2-propenyl group and the like, preferably a vinyl group.

The linear or branched $C_{2-4}$ alkenyl group represented by $R_1$, $R_2$, $R_7$, and $R_8$ is optionally substituted, and examples of the substituent thereof include at least one group selected from the group consisting of a halogen atom, a linear or branched $C_{1-4}$ alkoxy group, a linear or branched $C_{1-4}$ alkoxy group optionally substituted with a halogen atom, an optionally substituted aromatic hydrocarbon group, and an optionally substituted heterocyclic group, preferably at least one group selected from the group consisting of a halogen atom, a linear or branched $C_{1-4}$ alkoxy group optionally substituted with a halogen atom, and an optionally substituted aromatic hydrocarbon group. When two or more halogen atoms are present, they may be the same or different. Examples of the substituent of the aromatic hydrocarbon group and the heterocyclic group include at least one group selected from the group consisting of a halogen atom, a linear or branched $C_{1-4}$ alkyl group optionally substituted with a halogen atom, a linear or branched $C_{1-4}$ alkoxy group optionally substituted with a halogen atom, and an alkoxy group which is optionally substituted with a linear or branched $C_{1-4}$ alkoxy group optionally substituted with a halogen atom, preferably at least one group selected from the group consisting of a halogen atom, and a linear or branched $C_{1-4}$ alkyl group optionally substituted with a halogen atom.

Specific examples the optionally substituted linear or branched $C_{2-4}$ alkenyl group represented by $R_1$, $R_2$, $R_7$, and $R_8$ include, in addition to specific examples of the above-mentioned unsubstituted linear or branched $C_{2-4}$ alkenyl group, 1,2,2-trifluorovinyl, 3,3-difluoro-2-propan-1-yl, 3,3-dichloro-2-propan-1-yl, a 1-phenylethenyl group, a 2-phenylethenyl group and the like, preferably 3,3-dichloro-2-propan-1-yl.

The linear or branched $C_{2-4}$ alkynyl group represented by $R_1$, $R_2$, $R_7$, and $R_8$ may be either linear or branched, and represents a $C_{2-4}$ alkynyl group, preferably a linear or branched $C_{2-3}$ alkynyl group.

Specific examples of the linear or branched $C_{2-4}$ alkynyl group represented by $R_1$, $R_2$, $R_7$, and $R_8$ include an ethynyl group, a 1-propynyl group, a 2-propynyl group and the like, preferably a 1-propynyl group.

The linear or branched $C_{2-4}$ alkynyl group represented by $R_1$, $R_2$, $R_7$, and $R_8$ is optionally substituted, and examples of the substituent thereof include at least one group selected from the group consisting of a halogen atom, a linear or branched $C_{2-4}$ alkoxy group, a linear or branched $C_{1-4}$ alkoxy group optionally substituted with a halogen atom, an optionally substituted aromatic hydrocarbon group, and an optionally substituted heterocyclic group, preferably at least one group selected from the group consisting of a halogen atom, a linear or branched $C_{1-4}$ alkoxy group optionally substituted with a halogen atom, and an optionally substituted aromatic hydrocarbon group. When two or more halogen atoms are present, they may be the same or different. Examples of the substituent of the aromatic hydrocarbon group and the heterocyclic group include at least one group selected from the group consisting of a halogen atom, a linear or branched $C_{1-4}$ alkyl group optionally substituted with a halogen atom, a linear or branched $C_{1-4}$ alkoxy group optionally substituted with a halogen atom, and an alkoxy group which is optionally substituted with a linear or branched $C_{1-4}$ alkoxy group optionally substituted with a halogen atom, preferably at least one group selected from the group consisting of a halogen atom, and a linear or branched $C_{1-4}$ alkyl group optionally substituted with a halogen atom.

Specific examples of the optionally substituted linear or branched $C_{2-4}$ alkynyl group represented by $R_1$, $R_2$, $R_7$, and $R_8$ include, in addition to specific examples of the above-mentioned unsubstituted linear or branched $C_{2-4}$ alkynyl group, a phenylethynyl group, a (2-pyridyl)ethynyl group, (3-gyridyl)ethynyl, a (4-pyridyl)ethynyl group and the like, preferably a phenylethynyl group.

The $C_{3-8}$ cyclic aliphatic hydrocarbon group represented by $R_1$, $R_2$, $R_5$, $R_7$, and $R_8$ is not particularly limited as long as the number of carbon atoms is 3 to 8, and the number of carbon atoms is preferably 3 to 6, Specific examples of the $C_{3-8}$ cyclic aliphatic hydrocarbon group represented by $R_1$, $R_2$, $R_5$, $R_7$, and $R_8$ include a cyclopropyl group, a cyclobutyl group, a cyclopentyl group, a cyclohexyl group, a cycloheptyl group, a bicycloheptyl group, a cyclooctyl group, a bicyclooctyl group and the like, preferably a cyclopropyl group, a cyclobutyl group, a cyclopentyl group, or a cyclohexyl group.

The $C_{3-8}$ cyclic aliphatic hydrocarbon group represented by $R_1$, $R_2$, $R_5$, $R_7$, and $R_8$ is optionally substituted, and examples of the substituent thereof include at least one group selected from the group consisting of a linear or branched $C_{1-4}$ alkyl group, a halogen atom, and a linear or branched $C_{1-4}$ alkoxy group optionally substituted with a halogen atom, preferably a linear or branched $C_{1-4}$ alkoxy group optionally substituted with a halogen atom. When two or more halogen atoms are present, they may be the same or different.

Specific examples of the optionally substituted $C_{3-8}$ cyclic aliphatic hydrocarbon group represented by $R_1$, $R_2$, $R_5$, $R_7$, and $R_8$ include, in addition to specific examples of the above-mentioned unsubstituted $C_{3-8}$ cyclic aliphatic hydrocarbon group, a methylcyclopropyl group, an ethylcyclopropyl group, a propylcyclopropyl group, a methylcyclohexyl group, an ethylcyclohexyl group, a methoxycyclohexyl group, a trifluoromethoxycyclohexyl group and the like, preferably a methoxycyclohexyl group, or a trifluoromethoxycyclohexyl group.

The aromatic hydrocarbon group represented by $R_1$ and $R_2$ is optionally substituted, and examples of the substituent thereof include at least one group selected from the group consisting of a halogen atom, a linear or branched $C_{1-4}$ alkyl group optionally substituted with a halogen atom, a linear or branched $C_{1-4}$ alkoxy group optionally substituted with a halogen atom, and a phenoxy group which is optionally substituted with a linear or branched $C_{1-4}$ alkoxy group optionally substituted with a halogen atom (i.e., a phenoxy group is optionally substituted with a linear or branched $C_{1-4}$ alkoxy group, and the $C_{1-4}$ alkoxy group is optionally substituted with a halogen atom), preferably at least one group selected from the group consisting of a linear or branched $C_{1-4}$ alkyl group optionally substituted with a halogen atom, a linear or branched $C_{1-4}$ alkoxy group optionally substituted with a halogen atom, and a phenoxy group which is optionally substituted with a linear or branched $C_{1-4}$ alkoxy group optionally substituted with a halogen atom. When two or more halogen atoms are present, they may be the same or different.

Specific examples of the optionally substituted aromatic hydrocarbon group represented by $R_1$ and $R_2$ include a phenyl group, a methylphenyl group such as a 4-methylphenyl group, a chlorophenyl group such as a 2-chlorophenyl group or a 4-chlorophenyl group, a 3,4-dichlorophenyl group, a 2,4-dichlorophenyl group, a 3,4-difluorophenyl group, a 2,4-difluorophenyl group, a 4-bromophenyl group, a 4-trifluoromethylphenyl group, a 4-(trifluoromethoxy)phenyl group, a toluyl group such as a 4-toluyl group, a (4-(4-(trifluoromethoxy))phenoxy)phenyl group, a 4-methoxyphenyl group, a 4-bromo-2-chlorophenyl group, a naphthyl group, and the like, preferably a phenyl group, a 4-trifluoromethylphenyl group, a 4-(trifluoromethoxy)phenyl group, or a (4-(4-(trifluoromethoxy))phenoxy)phenyl group.

The heterocyclic group represented by $R_1$ and $R_2$ is optionally substituted, and examples of the substituent thereof include at least one group selected from the group consisting of a halogen atom, a linear or branched $C_{1-4}$ alkyl group optionally substituted with a halogen atom, and a linear or branched $C_{1-4}$ alkoxy group optionally substituted with a halogen atom, preferably at least one group selected from a halogen atom, and a linear or branched $C_{1-4}$ alkyl group optionally substituted with a halogen atom. When two or more halogen atoms are present, they may be the same or different.

Specific examples of the optionally substituted heterocyclic group represented by $R_1$ and $R_2$ include a pyridyl group, a pyrimidinyl group, a pyrazinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, a tetrazolyl group, a trifluoromethylpyridyl group, a trifluoromethylthienyl group, a trifluoromethylisoxazolyl group and the like, preferably a trifluoromethylpyridyl group.

Examples of the group —$(CH_2)_p$— (p is 2 to 6) represented by $R_1$ and $R_2$ combined together include a group —$(CH_2)_2$—, a group —$(CH_2)_3$—, a group —$(CH_2)_4$—, a group —$(CH_2)_5$—, a group —$(C_2)_6$— and the like, preferably a group —$(CH_2)_3$—, or a group —$(CH_2)_4$.

The linear or branched $C_{1-4}$ alkoxy group represented by $X_2$ represents a $C_{1-4}$ alkoxy group which may be either linear or branched, preferably a linear or branched $C_{1-3}$ alkoxy group.

Specific examples of the linear or branched $C_{1-4}$ alkoxy group represented by $X_2$ include a methoxy group, an ethoxy group, a propyloxy group, an i-propyloxy group, an n-butoxy group, an i-butoxy group, a s-butoxy group, a t-butoxy group and the like, preferably a methoxy group.

The linear or branched $C_{1-4}$ alkoxy group represented by $X_2$ is optionally substituted, and examples of the substituent thereof include at least one group selected from a halogen atom, a linear or branched $C_{1-4}$ alkoxy group, a linear or branched $C_{1-4}$ alkoxy group optionally substituted with a halogen atom, an optionally substituted aromatic hydrocarbon group, and an optionally substituted heterocyclic group, preferably at least one group selected from the group consisting of a halogen atom, and a linear or branched $C_{1-4}$ alkoxy group optionally substituted with a halogen atom. When two or more halogen atoms are present, they may be the same or different. Examples of the substituent of the aromatic hydrocarbon group and the heterocyclic group include at least one group selected from the group consisting of a halogen atom, a linear or branched $C_{1-4}$ alkyl group optionally substituted with a halogen atom, a linear or branched $C_{1-4}$ alkoxy group optionally substituted with a halogen atom, and an alkoxy group which is optionally substituted with a linear or branched $C_{1-4}$ alkoxy group optionally substituted with a halogen atom, preferably at least one group selected from the group consisting of a halogen atom, or a linear or branched $C_{1-4}$ alkyl group optionally substituted with a halogen atom, Specific examples of the optionally substituted linear or branched $C_{1-4}$ alkoxy group represented by $X_2$ include, in addition to specific examples of the above-mentioned unsubstituted linear or branched $C_{1-4}$ alkoxy group, a trifluoromethoxy group, a pentafluoroethoxy group and the like, preferably a trifluoromethoxy group.

Examples of the group —$(CH_2)_q$— (q is 3 to 7) represented by $R_3$ and $R_4$ combined together include a group —$(CH_2)_4$—, a group —$(CH_2)_5$—, a group —$(CH_2)_6$— and the like, preferably a group —$(CH_2)_4$— or a group —$(CH_2)_5$—.

k represents a numeral of 1 or more, and preferably 1 to 6.

l represents 1 or 2, and preferably 2.

m represents a numeral of 0 or more and preferably 0 to 2.

$R_6$ represents a hydrogen atom, a halogen atom, or —B—$R_7$.

B represents an oxygen atom, a sulfur atom, $N(R_8)$, $N(R_8)$—CO, or CO—$N(R_8)$.

The aromatic hydrocarbon group represented by $R_7$ and $R_8$ is optionally substituted, and examples of the substituent thereof include at least one group selected from a halogen atom, a linear or branched $C_{1-4}$ alkyl group optionally substituted with a halogen atom, a linear or branched $C_{1-4}$ alkyl group which is optionally substituted with a $C_{1-4}$ alkoxy group optionally substituted with a halogen atom, a linear or branched $C_{2-4}$ alkenyl group optionally substituted with a halogen atom, a linear or branched $C_{2-4}$ alkenyl group which is optionally substituted with a $C_{1-4}$ alkoxy group optionally substituted with a halogen atom, a linear or branched $C_{2-4}$ alkynyl group optionally substituted with a halogen atom, a linear or branched $C_{2-4}$ alkynyl group which is optionally substituted with a $C_{1-4}$ alkoxy group optionally substituted with a halogen atom, a linear or branched $C_{1-4}$ alkoxy group optionally substituted with a halogen atom, a linear or branched $C_{1-4}$ alkoxy group which is optionally substituted with a $C_{1-4}$ alkoxy group optionally substituted with a halogen atom, a linear or branched $C_{2-4}$ alkenyloxy group optionally substituted with a halogen atom, a linear or branched $C_{2-4}$ alkenyloxy group which is optionally substituted with a $C_{1-4}$ alkoxy group optionally substituted with a halogen atom, a linear or branched $C_{2-4}$ alkynyloxy group optionally substituted with a halogen atom, a linear or branched $C_{2-4}$ alkynyloxy group which is optionally substituted with a $C_{1-4}$ alkoxy group optionally substituted with a halogen atom, and a phenoxy group (e.g., a 4-(trifluoromethoxy)phenoxy group) which is optionally substituted with a $C_{1-4}$ alkoxy group optionally substituted with a halogen atom, preferably at least one group selected from the group consisting of a linear or branched $C_{1-4}$ alkyl group optionally substituted with a halogen atom, and a linear or branched $C_{1-4}$ alkoxy group optionally substituted with a halogen atom. When two or more halogen atoms are present, they may be the same or different Specific examples of the optionally substituted aromatic hydrocarbon group represented by $R_7$ and $R_8$ include a phenyl group, a methylphenyl group such as a 4-methylphenyl group, a chlorophenyl group such as a 2-chlorophenyl group or a 4-chlorophenyl group, a 3,4-dichlorophenyl group, a 2,4-dichlorophenyl group, a 3,4-difluorophenyl group, a 2,4-difluorophenyl group, a 4-bromophenyl group, a trifluoromethoxyphenyl group such as a 4-(trifluoromethoxy)phenyl group, a toluyl group such as a 4-toluyl group, a trifluoromethylphenyl group such as a 4-trifluoromethylphenyl group, methoxyphenyl group such as a 4-methoxyphenyl group, a 2-chloro-4-trifluoromethylphenyl group, a 3-chloro-4-trifluoromethylphenyl group, a 4-bromo-2-chlorophenyl group, a 4-(4-(trifluoromethoxy) phenoxy)phenyl group, a biphenyl-4-yl group, a 4-(1-butoxy)phenyl group, a naphthyl group, an anthracyl group, a phenanthryl group and the like, preferably a 4-(trifluoromethyl)phenyl group or a 4 trifluoromethoxy)phenyl group.

The heterocyclic group represented by $R_7$ and $R_8$ is optionally substituted, and examples of the substituent thereof include at least one group selected from a halogen atom, a linear or branched $C_{1-4}$ alkyl group optionally substituted with a halogen atom, a linear or branched $C_{1-4}$ alkyl group which is optionally substituted with a $C_{1-4}$ alkoxy group optionally substituted with a halogen atom, a linear or branched $C_{2-4}$ alkenyl group optionally substituted with a halogen atom, a linear or branched $C_{2-4}$ alkenyl group which is optionally substituted with a $C_{1-4}$ alkoxy group optionally substituted with a halogen atom, a linear or branched $C_{2-4}$ alkynyl group optionally substituted with a halogen atom, a linear or branched $C_{2-4}$ alkynyl group which is optionally substituted with a $C_{1-4}$ alkoxy group optionally substituted with a halogen atom, a linear or branched $C_{1-4}$ alkoxy group optionally substituted with a halogen atom, a linear or branched $C_{1-4}$ alkoxy group which is optionally substituted with a $C_{1-4}$ alkoxy group optionally substituted with a halogen atom, a linear or branched $C_{2-4}$ alkenyloxy group optionally substituted with a halogen atom, a linear or branched $C_{2-4}$ alkenyloxy group which is optionally substituted with a $C_{1-4}$ alkoxy group optionally substituted with a halogen atom, a linear or branched $C_{2-4}$ alkynyloxy group optionally substituted with a halogen atom, a linear or branched $C_{2-4}$ alkynyloxy group which is optionally substituted with a $C_{1-4}$ alkoxy group optionally substituted with a halogen atom, and a phenoxy group which is optionally substituted with a linear or branched $C_{1-4}$ alkoxy group optionally substituted with a halogen atom, preferably at least one group selected from the group consisting of a halogen atom, a linear or branched $C_{1-4}$ alkyl group optionally substituted with a halogen atom, and a $C_{1-4}$ alkoxy group optionally substituted with a halogen atom. When two or more halogen atoms are present, they may be the same or different.

Specific examples of the optionally substituted heterocyclic group represented by $R_7$ and $R_8$ include a pyridyl group, a pyrimidinyl group, a pyrazinyl group, a pyridazyl group, a furyl group, a thienyl group, an oxazolyl group, an isoxazolyl group, an oxadiazolyl group, a thiazolyl group, an isothiazolyl group, a thiadiazolyl group, a pyrrolyl group, an imidazolyl group, a triazolyl group, a pyrazolyl group, a tetrazolyl group, a trifluoromethylpyridyl group, a trifluoromethylthienyl group and the like, preferably a pyridyl group, a thienyl group, a trifluoromethylpyridyl group, or a trifluoromethylthienyl group.

As used herein "$C_{1-4}$ alkoxy group" means a linear or branched $C_{1-4}$ alkoxy group.

The $C_{1-4}$ alkoxy group and the linear or branched $C_{1-4}$ alkoxy group in $R_1$, $R_2$, $R_7$, and $R_8$ means a $C_{1-4}$ alkoxy group which may be either linear or branched, preferably a linear or branched $C_{1-3}$ alkoxy group.

Specific examples of the $C_{1-4}$ alkoxy group and the linear or branched $C_{1-4}$ alkoxy group in $R_1$, $R_2$, $R_7$, and $R_8$ include a methoxy group, an ethoxy group, a propyloxy group, an i-propyloxy group, an n-butoxy group, an i-butoxy group, a s-butoxy group, a t-butoxy group and the like, preferably a methoxy group.

The linear or branched $C_{1-4}$ alkyl group represented by $R_9$, $R_{10}$, $R_{11}$, $R_{12}$, and $R_{13}$ represents a $C_{1-4}$ alkyl group which may be either linear or branched, preferably a linear or branched $C_{1-3}$ alkyl group, Specific examples of the linear or branched $C_{1-4}$ alkyl group represented by $R_9$, $R_{10}$, $R_{11}$, $R_{12}$, and $R_{13}$ include a methyl group, an ethyl group, an n-propyl group, an i-propyl group, an n-butyl group, an i-butyl group, a s-butyl group, a t-butyl group and the like, preferably a methyl group, an ethyl group, an n-propyl group, or an i-propyl group.

The linear or branched $C_{1-4}$ alkyl group represented by $R_9$, $R_{10}$, $R_{11}$, $R_{12}$, and $R_{13}$ is optionally substituted, and examples of the substituent thereof include at least one group selected from the group consisting of a halogen atom, and a linear or branched $C_{1-4}$ alkoxy group optionally substituted with a halogen atom, preferably a halogen atom. When two or more halogen atoms are present, they may be the same or different.

Specific examples of the optionally substituted linear or branched $C_{1-4}$ alkyl group represented by $R_9$, $R_{10}$, $R_{11}$, $R_{12}$, and $R_{13}$ include, in addition to specific examples of the above-mentioned unsubstituted linear or branched $C_{1-4}$ alkyl group, a fluoromethyl group, a difluoromethyl group, a chlorodifluoromethyl group, a trifluoromethyl group, a pentafluoroethyl group, a heptafluoro-n-propyl group, a heptafluoro-i-propyl group, a 2,2,2-trifluoro-1-trifluoromethyl-1-methoxyethyl group, a chloromethyl group, a trichloromethyl group, a (1- or 2-)chloroethyl group, a 2,2,2-trifluoroethyl group, a 1,1,2,2-tetrafluoroethyl group, a pentafluoroethyl group, a methoxymethyl group, a 2-trifluoromethoxyethyl group and the like, preferably a difluoromethyl group, a chlorodifluoromethyl group, or a trifluoromethyl group.

The linear or branched $C_{2-4}$ alkenyl group represented by $R_9$, $R_{10}$, $R_{11}$, $R_{12}$, and $R_{13}$ represents a $C_{2-4}$ alkenyl group which may be either linear or branched, preferably a linear or branched $C_{2-3}$ alkenyl group.

Specific examples of the linear or branched $C_{2-4}$ alkenyl group represented by $R_9$, $R_{10}$, $R_{11}$, $R_{12}$, and $R_{13}$ include a vinyl group, a 1-propenyl group, a 2-propenyl group, a 1-methyl-1-propenyl group and the like, preferably a vinyl group, or a 1-propenyl group.

The linear or branched $C_{2-4}$ alkenyl group represented by $R_9$, $R_{10}$, $R_{11}$, $R_{12}$, and $R_{13}$ is optionally substituted, and examples of the substituent thereof include at least one group selected from the group consisting of a halogen atom, and a linear or branched $C_{1-4}$ alkoxy group optionally substituted with a halogen atom, preferably a halogen atom. When two or more halogen atoms are present, they may be the same or different.

Specific examples of the optionally substituted linear or branched $C_{2-4}$ alkenyl group represented by $R_9$, $R_{10}$, $R_{11}$, and $R_{13}$ include, in addition to specific examples of the above-mentioned unsubstituted linear or branched $C_{2-4}$ alkenyl group, a 3,3-dichloro-2-propenyl group, a 3,3-difluoro-2-propenyl group, a 1,2,2-trifluorovinyl group, a 1-trifluoromethyl-1-propenyl group and the like, preferably a 3,3-dichloro-2-propenyl group.

The linear or branched $C_{2-4}$ alkynyl group represented by $R_9$, $R_{10}$, $R_{11}$, $R_{12}$, and $R_{13}$ represents a $C_{2-4}$ alkynyl group which may be either linear or branched, preferably a linear or branched $C_{2-3}$ alkynyl group.

Specific examples of the linear or branched $C_{2-4}$ alkynyl group represented by $R_9$, $R_{10}$, $R_{11}$, $R_{12}$, and $R_{13}$ include an ethynyl group, a 1-propynyl group, 2-propynyl group and the like, preferably a 1-propynyl group.

The linear or branched $C_{2-4}$ alkynyl group represented by $R_9$, $R_{10}$, $R_{11}$, $R_2$, and $R_{13}$ is optionally substituted, and examples of the substituent thereof include at least one group selected from the group consisting of a halogen atom, and a linear or branched $C_{1-4}$ alkoxy group optionally substituted with a halogen atom, preferably a halogen atom. When two or more halogen atoms are present, they may be the same or different.

Specific examples of the optionally substituted linear or branched $C_{2-4}$ alkynyl group represented by $R_9$, $R_{10}$, $R_{11}$, $R_{12}$, and $R_{13}$ include, in addition to specific examples of the above-mentioned unsubstituted linear or branched $C_{2-4}$ alkynyl group, a 2-fluoroethynyl group, a 3,3,3-trifluoro-1-propynyl group and the like, preferably a 2-fluoroethynyl group.

The linear or branched $C_{1-4}$ alkoxy group represented by $R_9$, $R_{10}$, $R_{11}$, $R_{12}$, and $R_{13}$ represents a $C_{1-4}$ alkoxy group which may be either linear or branched, preferably a linear or branched $C_{1-3}$ alkoxy group.

Specific examples of the linear or branched $C_{1-4}$ alkoxy group represented by $R_9$, $R_{10}$, $R_{11}$, $R_{12}$, and $R_{13}$ include a methoxy group, an ethoxy group, an n-propyloxy group, an i-propyloxy group, an n-butoxy group, an i-butoxy group, a s-butoxy group, a t-butoxy group and the like, preferably a methoxy group, or an ethoxy group.

The linear or branched $C_{1-4}$ alkoxy group represented by $R_9$, $R_{10}$, $R_{11}$, $R_{12}$, and $R_{13}$ is optionally substituted, and examples of the substituent thereof include at least one group selected from the group consisting of a halogen atom, and a linear or branched $C_{1-4}$ alkoxy group optionally substituted with a halogen atom, preferably a halogen atom. When two or more halogen atoms are present, they may be the same or different.

Specific examples of the optionally substituted linear or branched $C_{1-4}$ alkoxy group represented by $R_9$, $R_{10}$, $R_{11}$, $R_{12}$, and $R_{13}$ include, in addition to specific examples of the above-mentioned unsubstituted linear or branched $C_{1-4}$ alkoxy group, a fluoromethoxy group, a difluoromethoxy group, a chlorodifluoromethoxy group, a trifluoromethoxy group, a 2,2,2-trifluoroethoxy, a 2,2,3,3,3-trifluoro-n-propyloxy group and the like, preferably a trifluoromethoxy group.

The linear or branched $C_{2-4}$ alkenyloxy group represented by $R_9$, $R_{10}$, $R_{11}$, $R_{12}$, and $R_{13}$ represents a $C_{2-4}$ alkenyloxy group which may be either linear or branched, preferably a linear or branched $C_{2-3}$ alkenyloxy group.

Specific examples of the linear or branched $C_{2-4}$ alkenyloxy group represented by $R_9$, $R_{10}$, $R_{11}$, $R_{12}$, and $R_{13}$ include a vinyloxy group, a 1-propenyloxy group, a 2-propenyloxy group, a 1-methyl-1-propenyloxy group and the like, preferably a 2-propenyloxy group.

The $C_{2-4}$ alkenyloxy group represented by $R_9$, $R_{10}$, $R_{11}$, $R_{12}$, and $R_{13}$ is optionally substituted, and examples of the substituent thereof include at least one group selected from the group consisting of a halogen atom, and a linear or branched $C_{1-4}$ alkoxy group optionally substituted with a halogen atom, preferably a halogen atom. When two or more halogen atoms are present, they may be the same or different.

Specific examples of the optionally substituted linear or branched $C_{2-4}$ alkenyloxy group represented by $R_9$, $R_{10}$, $R_{11}$, $R_{12}$, and $R_{13}$ include, in addition to specific examples of the above-mentioned unsubstituted linear or branched $C_{2-4}$ alkenyloxy group, a 3,3-dichloro-2-propenyloxy group, a 3,3-difluoro-2-propenyloxy group, a 1,2,2-trifluorovinyloxy group, a 1-trifluoromethyl-1-propenyloxy group and the like, preferably a 3,3-dichloro-2-propenyloxy group.

The linear or branched $C_{2-4}$ alkynyloxy group represented by $R_9$, $R_{10}$, $R_{11}$, $R_{12}$, and $R_{13}$ represents a $C_{2-4}$ alkynyloxy group which may be either linear or branched, preferably a linear or branched $C_{2-3}$ alkynyloxy group.

Specific examples of the linear or branched $C_{2-4}$ alkynyloxy group represented by $R_9$, $R_{10}$, $R_{11}$, $R_{12}$, and $R_{13}$ include an ethynyloxy group, a 1-propynyloxy group, a 2-propynyloxy group and the like, preferably a 2-propynyloxy group.

The linear or branched $C_{2-4}$ alkynyloxy group represented by $R_9$, $R_{10}$, $R_{11}$, $R_{12}$, and $R_{13}$ is optionally substituted, and examples of the substituent thereof include at least one group selected from the group consisting of a halogen atom, and a linear or branched $C_{1-4}$ alkoxy group optionally substituted with a halogen atom, preferably a halogen atom. When two or more halogen atoms are present, they may be the same or different.

Specific examples of the optionally substituted linear or branched $C_{2-4}$ alkynyloxy group represented by $R_9$, $R_{10}$, $R_{11}$, $R_{12}$, and $R_{13}$ include, in addition to specific examples of the above-mentioned unsubstituted linear or branched $C_{2-4}$ alkynyloxy group, a 2-fluoroethynyloxy group, a 3,3,3-trifluoro-1-propynyloxy group and the like, preferably a 3,3,3-trifluoro-1-propynyloxy group.

$R_1$ in general formula (2), general formula (7), and general formula (9) is preferably a linear or branched $C_{1-4}$ alkyl group or an aromatic hydrocarbon group, more preferably a linear or branched $C_{1-3}$ alkyl group, and still more preferably a methyl group or an ethyl group.

$R_2$ in general formula (2), general formula (7), and general formula (9) is preferably a linear or branched $C_{1-4}$ alkyl group or an optionally substituted aromatic hydrocarbon group, more preferably a linear or branched $C_{1-3}$ alkyl group, or an aromatic hydrocarbon group optionally substituted with a 4-(trifluoromethoxy)phenoxy group, and still more preferably a methyl group or a 4-(4-(trifluoromethoxy)phenoxy)phenyl group.

$R_3$ and $R_4$ in general formula (4 are preferably combined together to represent a group —$(CH_2)_q$— (q is 3 to 7) and l is 1 or 2, or both are a methyl group and l is 1 or 2, more preferably combined together to represent a group —$(CH_2)_q$— (q is 4 to 6) and l is 1 or 2, or both are a methyl group and l is 1 or 2, and still more preferably combined together to represent a group —$(CH_2)_4$— or a group —$(CH_2)_5$— and l is 2, or both are a methyl group and l is 2.

$R_5$ in general formula (6) and general formula (8) is preferably a linear or branched $C_{1-4}$ alkyl group, or a $C_{3-6}$ cyclic aliphatic hydrocarbon group, more preferably a linear or branched $C_{1-3}$ alkyl group, or a $C_{4-6}$ cyclic aliphatic hydrocarbon group, and still more preferably a methyl group, an ethyl group, a propyl group, or an i-propyl group.

$R_6$ in general formula (6) and general formula (7) is preferably a halogen atom or —B—$R_7$, in which B is preferably an oxygen atom, or a sulfur atom.

$R_7$ in general formula (6) and general formula (7) is preferably an optionally substituted aromatic hydrocarbon group, more preferably an aromatic hydrocarbon group which is optionally substituted with a linear or branched $C_{1-4}$ alkyl group optionally substituted with a halogen atom, an aromatic hydrocarbon group which is optionally substituted with a linear or branched $C_{1-4}$ alkoxy group optionally substituted with a halogen atom, or an aromatic hydrocarbon group which is optionally substituted with a phenoxy group (e.g., a 4-(trifluoromethoxy)phenoxy group) which is optionally substituted with a $C_{1-4}$ alkoxy group optionally substituted with a halogen atom, and still more preferably a 4-(trifluoromethyl)phenyl group, a 4-(trifluoromethoxy)phenyl group, or a 4-(4-(trifluoromethoxy)phenoxy)phenyl group.

$R_8$ in general formula (6) and general formula (7) is preferably a hydrogen atom, or an optionally substituted linear or branched $C_{1-4}$ alkyl group, and more preferably a hydrogen atom.

$X_2$ in general formula (6), general formula (8), and general formula (9) is preferably an optionally substituted linear or branched $C_{1-4}$ alkyl group, or an optionally substituted linear or branched $C_{1-4}$ alkoxy group, more preferably an optionally substituted linear or branched $C_{1-3}$ alkyl group, and still more preferably a methyl group or a trifluoromethyl group.

$R_9$ in general formula (8) and general formula (9) is preferably a hydrogen atom, or a linear or branched $C_{1-4}$ alkyl group, and more preferably a hydrogen atom.

$R_{10}$ in general formula (8) and general formula (9) is preferably a hydrogen atom, or a linear or branched $C_{1-4}$ alkyl group, and more preferably a hydrogen atom.

$R_{11}$ in general formula (8) and general formula (9) is preferably a linear or branched $C_{1-4}$ alkyl group optionally substituted with a halogen atom, or a linear or branched $C_{1-4}$ alkoxy group optionally substituted with a halogen atom, more preferably a linear or branched $C_{1-3}$ alkyl group optionally substituted with a halogen atom, or a linear or branched $C_{1-3}$ alkoxy group optionally substituted with a halogen atom, and still more preferably a trifluoromethyl group or a trifluoromethoxy group.

$R_{12}$ in general formula (8) and general formula (9) is preferably a hydrogen atom, or a linear or branched $C_{1-4}$ alkyl group, and more preferably a hydrogen atom.

$R_{13}$ in general formula (8) and general formula (9) is preferably a hydrogen atom, or a linear or branched $C_{1-4}$ alkyl group, and more preferably a hydrogen atom.

According to a preferred embodiment of the combination of substituents Z, $R_1$ $R_8$, and $X_2$, Z represents a halogen atom, $R_1$ and $R_2$ each independently represent:

an optionally substituted linear or branched $C_{1-4}$ alkyl group, an optionally substituted linear or branched $C_{2-4}$ alkenyl group, or an optionally substituted linear or branched $C_{2-4}$ alkynyl group, wherein each of the substituents in the linear or branched $C_{1-4}$ alkyl group, the linear or branched $C_{2-4}$ alkenyl group, and the linear or branched $C_{2-4}$ alkynyl group is a halogen atom, or a $C_{1-4}$ alkoxy group optionally substituted with a halogen atom, $R_3$ and $R_4$ are combined together to represent a group —$(CH_2)_q$— (q is 3 to 7), l represents 1 or 2, $R_5$ represents a linear or branched $C_{1-4}$ alkyl group, $R_6$ represents a hydrogen atom, a halogen atom, or —B—$R_7$, wherein B represents an oxygen atom, sulfur atom, $N(R_8)$, $N(R_8)$—CO, or CO—$N(R_8)$, $R_7$ and $R_8$ each independently represent a halogen atom, or an aromatic hydrocarbon group which is optionally substituted with a linear or branched $C_{1-4}$ alkoxy group optionally substituted with a halogen atom, and $X_2$ represents a hydrogen atom, a halogen atom, a linear or branched $C_{1-4}$ alkyl group optionally substituted with a halogen atom, or a linear or branched $C_{1-4}$ alkoxy group optionally substituted with a halogen atom.

According to another preferred embodiment of the combination of substituents Z, $R_1$ to $R_8$, and $X_2$, Z represents a halogen atom, $R_1$ and $R_2$ each independently represent:

an optionally substituted linear or branched $C_{1-4}$ alkyl group, wherein the substituent in the linear or branched $C_{1-4}$ alkyl group is a halogen atom, or a $C_{1-4}$ alkoxy group optionally substituted with a halogen atom, $R_3$ and $R_4$ are combined together to represent a group —$(CH_2)_q$— (q is 4 to 6), l represents 1 or 2, $R_5$ represents a linear or branched $C_{1-4}$ alkyl group, $R_6$ represents —B—$R_7$, wherein B represents an oxygen atom, a sulfur atom, $N(R_8)$ $N(R_8)$—CO, or CO—$N(R_8)$, $R_7$ and $R_8$ each independently represent a halogen atom, or an aromatic hydrocarbon group which is substituted with a linear or branched $C_{1-4}$ alkoxy group optionally substituted with a halogen atom, and $X_2$ represents a linear or branched $C_{1-4}$ alkyl group optionally substituted with a halogen atom, or a linear or branched $C_{1-4}$ alkoxy group optionally substituted with a halogen atom.

According to still another preferred embodiment of the combination of substituents Z, $R_1$ to $R_8$, and $X_2$, Z represents fluorine, chlorine, or bromine, $R_1$ and $R_2$ each independently represent a methyl group, an ethyl group, a trifluoromethyl group, or are combined together to form a group —$(CH_2)_3$—, or are combined together to represent a group —$(CH_2)_4$—, $R_3$ and $R_4$ are combined together to represent a group —$(CH_2)_4$—, l represents 2, $R_5$ represents a methyl group, an ethyl group, an n-propyl group, or an i-propyl group, $R_6$ represents O—$R_7$, $R_7$ represents a 4-(trifluoromethoxy)phenyl group, or a 4-trifluoromethylphenyl group, and $X_2$ represents a methyl group, an ethyl group, a methoxy group, an ethoxy group, a trifluoromethyl group, or a trifluoromethoxy group.

According to a preferred embodiment of the combination of substituents Z, $R_1$ to $R_5$, $R_9$ to $R_{13}$, and $X_2$, Z represents a halogen atom, $R_1$ and $R_2$ each independently represent:

an optionally substituted linear or branched $C_{1-4}$ alkyl group, an optionally substituted linear or branched $C_{2-4}$ alkenyl group, or, an optionally substituted linear or branched $C_{2-4}$ alkynyl group, wherein each of the substituents in the linear or branched $C_{1-4}$ alkyl group, the linear or branched $C_{2-4}$ alkenyl group, and the linear or branched $C_{2-4}$ alkynyl group is a halogen atom, or a $C_{1-4}$ alkoxy group optionally substituted with a halogen atom, $R_3$ and $R_4$ are combined together to represent a group —$(CH_2)_q$— (q is 3 to 7), l represents 1 or 2, $R_5$ represents a linear or branched $C_{1-4}$ alkyl group, $R_9$, $R_{10}$, $R_{11}$, $R_{12}$, and $R_{13}$ each independently represent:

a hydrogen atom, an optionally substituted linear or branched $C_{1-4}$ alkyl group, or an optionally substituted linear or branched $C_{1-4}$ alkoxy group, wherein each of the substituents in the linear or branched $C_{1-4}$ alkyl group, and the optionally substituted linear or branched $C_{1-4}$ alkoxy group is a halogen atom, or a $C_{1-4}$ alkoxy group optionally substituted with a halogen atom, and $X_2$ represents a hydrogen atom, a halogen atom, a $C_{1-4}$ alkyl group optionally substituted with a halogen atom, or a $C_{1-4}$ alkyl group which is optionally substituted with a $C_{1-4}$ alkoxy group optionally substituted with a halogen atom.

According to another preferred embodiment of the combination of substituents Z, $R_1$ to $R_5$, $R_9$ to $R_{13}$, and $X_2$, Z represents a halogen atom, $R_1$ and $R_2$ each independently represent:

an optionally substituted linear or branched $C_{1-4}$ alkyl group, wherein the substituent in the linear or branched $C_{1-4}$ alkyl group is a halogen atom, or a $C_{1-4}$ alkoxy group optionally substituted with a halogen atom, $R_3$ and $R_4$ are combined together to represent a group —$(CH_2)_q$— (q is 4 to 6), l represents 1 or 2, $R_5$ represents a linear or branched $C_{1-4}$ alkyl group, $R_9$, $R_{10}$, $R_{11}$, $R_{12}$, and $R_{13}$ each independently represent:

a hydrogen atom, or an optionally substituted linear or branched $C_{1-4}$ alkyl group, or an optionally substituted linear or branched $C_{1-4}$ alkoxy group, wherein each of the substituents in the optionally substituted linear or branched $C_{1-4}$ alkyl group, and the optionally substituted linear or branched $C_{1-4}$ alkoxy group represents a halogen atom, a $C_{1-4}$ alkyl group optionally substituted with a halogen atom, or a $C_{1-4}$ alkoxy group optionally substituted with a halogen atom, and $X_2$ represents a linear or branched $C_{1-4}$ alkyl group optionally substituted with a halogen atom, or a linear or branched $C_{1-4}$ alkoxy group optionally substituted with a halogen atom.

According to still another preferred embodiment of the combination of substituents Z, $R_1$ to $R_5$, $R_9$ to $R_{13}$, and $X_2$, Z represents chlorine, $R_1$ and $R_2$ each independently represent a methyl group, an ethyl group, a trifluoromethyl group, or are combined together to represent a group —$(CH_2)_3$—, or are combined together to represent a group —$(CH_2)_4$—, $R_3$ and $R_4$ are combined together to represent a group —$(CH_2)_4$—, l represents 2, $R_5$ represents a methyl group, an ethyl group, an n-propyl group, or an i-propyl group, $R_9$, $R_{10}$, $R_{11}$, $R_{12}$, and $R_{13}$ each independently represent a hydrogen atom, a methyl group, a methoxy group, a trifluoromethyl group, or a trifluoromethoxy group, and $X_2$ represents a methyl group, an ethyl group, a methoxy group, an ethoxy group, a trifluoromethyl group, or a trifluoromethoxy group.

Production Method According to Present Invention

The production method according to the present invention includes a reaction step in which, using an aluminum halide represented by general formula (1) and, if necessary, a sulfide represented by general formula (4), a ketone represented by general formula (2) is reacted with an anthranilic acid derivative represented by general formula (6) to obtain a quinolone derivative represented by general formula (7). The reaction step is a cyclization reaction step. Moreover, the production method according to the present invention preferably includes a post-treatment step in which, after completion of the reaction, an aluminum halide represented by general formula (1) is removed to obtain a quinolone derivative represented by general formula (7).

In the production method according to the present invention, although there is no particular limitation as long as the effects of the present invention are not impaired, in the reaction step in which a ketone represented by general formula (2) is reacted with an anthranilic acid derivative represented by general formula (6) to obtain a quinolone derivative represented by general formula (7), an aluminum halide represented by general formula (1) and a ketone represented by general formula (2) and, if necessary, a sulfide represented by general formula (4) are preferably mixed in advance. Thereafter, the mixture thus obtained is preferably reacted with an anthranilic acid derivative represented by general formula (6). The temperature during mixing is not particularly limited and includes 0 to 40° C., and is preferably 10° C. to 30° C. The mixing time is not particularly limited and includes 0.1 to 2 hours, and is preferably 0.5 to 1 hour. It is possible to obtain an aluminum halide mixture represented by general formula (3) by mixing an aluminum halide represented by general formula (1) in advance with a ketone represented by general formula (2). It is also possible to obtain an aluminum halide mixture represented by general formula (5) by mixing an aluminum halide represented by general formula (1), a ketone represented by general formula (2), and a sulfide represented by general formula (4) in advance.

As mentioned above, an aluminum halide represented by general formula (1) and a ketone represented by general formula (2) and, if necessary, a sulfide represented by general formula (4) are mixed in advance, thus making it possible to appropriately control the reactivity of the aluminum halide represented by general formula (1) and to suppress by-products, leading to a notable improvement in yield.

Therefore, an aluminum halide represented by general formula (1) is mixed in advance with a ketone represented by general formula (2) and, if necessary, the mixture thus obtained is further mixed with a sulfide represented by general formula (4), thus making it possible to produce and isolate a quinolone derivative represented by general formula (7) with high yield and high selectivity, and to reduce the raw material.

In the present invention, in order to improve the yield, it is preferable to specify the combination of the order of adding each compound and/or the amount of each raw material used.

According to the production method of the present invention, in the reaction step, mixing of an aluminum halide represented by general formula (1) in advance with an excess amount of a ketone represented by general formula (2) is preferable, which is advantageous in that the reactivity is appropriately controlled and side reactions are suppressed, and the desired reaction is performed with high selectivity. Mixing of the aluminum halide represented by general formula (1) in advance with an excess amount of the ketone represented by general formula (2) enables the aluminum halide represented by general formula (1) to extremely strongly activate the cyclization reaction between the ketone represented by general formula (2) and the anthranilic acid derivative represented by general formula (6), which is advantageous in that various side reactions caused by the excessively strong reactivity can be prevented and a decrease in desired reaction yield can be prevented.

In the present invention, replacement of a par of an excess amount of a ketone represented by general formula (2), which is a relatively expensive main raw material, by a sulfide represented by general formula (4), which is inert to the cyclization reaction itself, is more preferable, which is advantageous in that it is possible to achieve an inexpensive and industrially suitable production method.

In the production method, according to the present invention, the order of adding each compound in the reaction step is not particularly limited as long as the effects of the present invention are not impaired, and it is preferable to add an aluminum halide represented by general formula (1), a solvent, a ketone represented by general formula (2) and, if necessary, a sulfide represented by general formula (4), and an anthranilic acid derivative represented by general formula (6) in this order. In this case, as long as the effects are not impaired, as mentioned below, it is preferable that the aluminum halide represented by general formula (1) is used in a given amount or less, or each amount of the ketone represented by general formula (2) and, if necessary, the sulfide represented by general formula (4) is limited to a given amount or more in that it is possible to prevent the anthranilic acid derivative represented by general formula (6) from being rapidly decomposed during the heating reaction leading to significant decrease in yield.

According to another embodiment of the production method of the present invention, the addition of a mixture of an aluminum halide represented by general formula (1) and a ketone represented by general formula (2) separately mixed, or a mixture of an aluminum halide represented by general formula (1), a ketone represented by general formula (2) and a sulfide represented by general formula (4) in the middle of the reaction step is also preferable in view of improving the yield.

It is also possible that, by changing the order of addition, an aluminum halide represented by general formula (1), a solvent, an anthranilic acid derivative represented by general formula (6), a ketone represented by general formula (2) and, if necessary, a sulfide represented by general formula (4) are added in this order and then a reaction is performed. In the case of this order, the anthranilic acid derivative represented by general formula (6) is rapidly hydrolyzed to the corresponding anthranilic acid, and less influence is exerted on the yield even when the reaction, rate is significantly reduced. This is because the hydrolyzed anthranilic acid also reacts with the ketone represented by general formula (2) to give a quinolone derivative represented by general formula (7) as a target product. In the reaction in this order of addition, it is preferable that the anthranilic acid derivative represented by general formula (6) does not have an alkoxy group or a haloalkoxy group as a substituent. The absence of such a substituent is advantageous in avoiding the side reaction of dealkylation or dehaloalkylation by the action of the aluminum halide represented by general formula (1), or preventing the yield from being significantly reduced.

Specific examples of the aluminum halide represented by general formula (1) include aluminum fluoride, aluminum chloride, aluminum bromide, aluminum iodide and the like, preferably aluminum chloride or aluminum bromide.

Specific examples of the ketone represented by general formula (2) include acetone, 2-butanone, 3-methyl-2-butanone, 3,3-dimethyl-2-butanone, 3-pentanone, 2-methyl-3-pentanone, 2,2-dimethyl-3-pentanone, 2,4-dimethyl-3-pentanone, acetophenone, propiophenone, 1-phenyl-2-propanone, 1-phenyl-2-butanone, cyclopentanone, cyclohexanone, cycloheptanone, cyclooctanone, 1-(4-(4-(trifluoromethoxy)phenoxy)phenyl)acetone and the like, preferably 2-butanone, 3-pentanone, cyclopentanone, or cyclohexanone.

Specific examples of the sulfide represented by general formula (4) include dimethyl sulfoxide, tetrahydrothiophene-1,1-dioxide and the like, preferably tetrahydrothiophene-1,1-dioxide.

The amount of the aluminum halide represented by general formula (1) used is not particularly limited as long as the effects of the present invention are not impaired and is, for example, 1.0- to 2,5-fold mol, and preferably 1.2- to 2.0-fold mol, relative to the anthranilic acid derivative represented by general formula (6).

The amount of the ketone represented by general formula (2) used is not particularly limited as long as the effects of the present invention are not impaired and is, for example, 0.5-fold mol or more, and preferably 0.8- to 3.0-fold mol, relative to the aluminum halide represented by general formula (1). When the aluminum halide represented by general formula (1) is mixed in advance with the ketone represented by general formula (2), the amount of the ketone represented by general formula (2) used is, for example, 0.5-fold mol or more, and preferably 0.8- to 3.0-fold mol. When the aluminum halide represented by general formula (1), the ketone represented by general formula (2), and the sulfide represented by general formula (4) are mixed in advance, the amount of the ketone is, for example, 0.5-fold mol or more, and preferably 0.8- to 3.0-fold mol. When the cyclization reaction is performed using the aluminum halide mixture represented by general formula (3), the amount of the ketone represented by general formula (2) used is, for example, 0.5-fold mol or more, and preferably 0.8- to 3.0-fold mol. When the cyclization reaction is performed using the aluminum halide mixture represented by general formula (5), the amount is, for example, 1.0-fold mol or more, and preferably 0.8- to 3.0-fold mol.

The amount of the sulfide represented by general formula (4) used is not particularly limited as long as the effects of the present invention are not impaired and is, for example, 0- to 2.0-fold mol, and preferably 0.5- to 1.5-fold mol, relative to the aluminum halide represented by general formula (1).

When the cyclization reaction is performed using the aluminum halide mixture represented by general formula (5), examples of the combination of numerical values represented by k, l and m include the combination in which the sum of the numerical value of the product of l and m and the numerical value of k is 2.0 or more, preferably 2.0 to 6.0. The combination in which the numerical value of k is more than or equal to the value of the product of l and m is more preferable.

When the aluminum halide mixture represented by general formula (3) is added in the reaction step, it is preferable to use a mixture obtained by separately mixing the aluminum halide represented by general formula (1) with the ketone represented by general formula (2). The amount of the aluminum halide represented by general formula (1) used in the mixture to be added is, for example, 1.5 to 2.5-fold mol, and preferably 13 to 2.3-fold mol, together with the amount of the aluminum halide used previously, relative to the aluminum halide represented by general formula (6). The mixture to be added may be added in a plurality of times as necessary.

When the ketone is added in the reaction step, the amount of the ketone represented by general formula (2) used in the mixture to be added is, for example, 0.8-fold mol or more, and preferably 0.9- to 4.0-fold mol, together with the amount of the ketone used previously, relative to the aluminum halide represented by general formula (1). When the aluminum halide represented by general formula (1) is mixed in advance with the ketone represented by general formula (2), the amount of the ketone represented by general formula (2) used is, for example, 0.8-fold mol or more, and preferably 0.9- to 4.0-fold mol, together with the amount of the ketone used previously. When the aluminum halide represented by general formula (1), the ketone represented by general formula (2), and the sulfide represented by general formula (4) are mixed in advance, the amount of the ketone is, for example, 0.8-fold mol or more, and preferably 0.9- to 4.0-fold mol, together with the amount of the ketone used previously. When the cyclization reaction is performed using the aluminum halide mixture represented by general formula (3), the amount of the ketone represented by general formula (2) used is, for example, 0.8-fold mol or more, and preferably 0.9- to 4,0-fold mol, together with the amount of the ketone used previously. When the cyclization reaction is performed using the aluminum halide mixture represented by general formula (5), the amount of the ketone is, for example, 0.8-fold mol or more, and preferably 0.9- to 4.0-fold mol, together with the amount of the ketone used previously. The ketone to be added may be added in a plurality of times as necessary.

When the sulfide is added in the reaction step, the amount of the sulfide represented by general formula (4) used in the mixture to be added is, for example, 0.5-fold mol or more, and preferably 0.5- to 1.5-fold mol, together with the amount of the sulfide used previously, relative to the total amount of the aluminum halide represented by general formula (1). The sulfide to be added may be added in a plurality of times as necessary.

According to the production method of the present invention, the reaction step can be performed in the presence or absence of a solvent. The solvent used is not particularly limited as long as it does not inhibit the reaction. These solvents may be used alone or in combination as a mixed solvent, and the solvent is preferably used alone from the viewpoint of recovery and reuse of the solvent. Examples of the solvent used in the production method of the present invention include aromatic hydrocarbons such as benzene, toluene, xylene, ethylbenzene, mesitylene, biphenyl, and diphenyl ether; halogenated aromatic hydrocarbons such as chlorobenzene and dichlorobenzene; aliphatic hydrocarbons such as cyclohexane and methylcyclohexane; halogenated aliphatic hydrocarbons such as dichloromethane, chloroform, and 1,2-dichloroethan, preferably toluene, xylene, or mesitylene.

The amount of the solvent used is, for example, 1,000 to 5,000 mL, preferably 1,500 to 3,000 mL, and more preferably 1,800 to 2,200 mL, relative to 1 mol of the anthranilic acid derivative represented by general formula (6).

The reaction step in the production method of the present invention is not particularly limited as long as the effects of the present invention are not impaired. Using an aluminum halide represented by general formula (1), a ketone represented by general formula (2) is preferably brought into contact with an anthranilic acid derivative represented by general formula (6) in a liquid phase. For example, the cyclization reaction is performed under normal pressure, under pressure or under reduced pressure by a method in which the ketone represented by general formula (2), the anthranilic acid derivative represented by general formula (6) and a solvent are mixed, followed by heating under reflux. The reaction temperature during contacting includes a reflux temperature of the solvent used, and is preferably 100 to 200° C., and more preferably 130 to 160° C. The contact time is not particularly limited as long as the effects of the present invention are not impaired, and includes 1 to 40 hours, preferably 6 to 30 hours. The contact may be performed once or a plurality of times.

In the production method of the present invention, water and an alcohol $R_5$—OH are by-produced as reaction by-products in the amount of 1.0-fold mol relative to the anthranilic acid derivative represented by general formula (6). These by-produced water and alcohol deactivate the aluminum halide mixture represented by general formulas (3) and (5) and inhibit the reaction, so that it is preferable to appropriately distill off by-produced water and alcohol together with the solvent corresponding to the progress of the reaction.

The amount of the solution distilled off is not particularly limited and is, for example, an amount in which a difference between the amount of the solvent used for the reaction and the amount of the solution to be distilled off becomes 100 to 1,000 mL, and preferably 300 to 700 mL, relative to 1 mol of the anthranilic acid derivative represented by general formula (6).

After completion of the reaction step, the quinolone derivative represented by general formula (7) can be isolated by removing the aluminum halide represented by general formula (1) by performing washing, extraction, precipitation, filtration, centrifugation, etc., or a post-treatment step of a combination thereof. The aluminum halide represented by general formula (1) after the reaction is easily soluble in strongly acidic water having a pH of 3 or lower or strongly basic water having a pH of 11 or more. The post-treatment step can be performed under conditions where strongly acidic or basic water is present, but is preferably performed under conditions where strongly basic water is present. When the quinolone derivative represented by general formula (7) is soluble in the reaction solvent and/or the extraction solvent, it is possible to obtain a quinolone derivative represented by general formula (7) containing no aluminum halide represented by general formula (1) as a solid crystal by distilling off the solvents after the extraction operation. Meanwhile, when the quinolone derivative represented by general formula (7) is slightly soluble in the reaction solvent and other organic solvents, it is possible to obtain a quinolone derivative represented by general formula (7) containing no aluminum halide represented by general formula (1) as a solid crystal by performing washing, sedimentation, filtration, etc. using an alcohol as an auxiliary solvent in the presence of hydrochloric acid or an aqueous caustic solution. For example, it is possible to obtain a quinolone derivative represented by general formula (7) containing no aluminum halide represented by general formula (1) as a solid crystal by washing using an alcohol as an auxiliary solvent in the presence of hydrochloric acid or an, aqueous caustic solution (preferably in the presence of an aqueous caustic solution), followed by extraction, washing, sedimentation, and filtration.

The method for isolating the quinolone derivative represented by general formula (7) by the above post-treatment step includes, for example, a method to be performed under acidic conditions, which will be mentioned as an example.

Water or a diluted hydrochloric acid solution is added to the reaction solution obtained in the reaction step, or the reaction solution is added to water or a diluted hydrochloric acid solution and then an alcohol is added, followed by heating and washing, cooling to room temperature or lower, and further filtration to remove crystals of the quinolone derivative. Moreover, the crystals may be washed with an aqueous alcohol solution as necessary.

The temperature during heating and washing is, for example, 40 to 100° C., and preferably 60 to 80° C. The time during heating and washing is, for example, 0.1 to 3.0 hours, and preferably 0.5 to 1.5 hours.

The alcohol used for heating and washing is not particularly limited as long as the effects of the present invention are not impaired, and methanol is preferable from the viewpoint of the economy. The amount thereof used is 500 to 1,500 mL, and preferably 750 to 1,000 mL, relative to 1 mol of the anthranilic acid derivative represented by general formula (6) in order to prevent dissolution of a target product in the filtrate and to prevent a decrease in yield.

The method for isolating the quinolone derivative represented by general formula (7) by the above post-treatment step includes, for example, a method to be performed under basic conditions, which will be mentioned as an example. Performing under basic conditions is advantageous in that the quinolone derivative represented by general formula (7 can be isolated under general industrial facility requirements.

An aqueous caustic solution is added to the reaction solution obtained in the reaction step, or the reaction solution is added to the aqueous caustic solution and then an alcohol is added, followed by heating and washing, the addition of water, and further heating and washing. Thereafter, the reaction mixture is cooled to 0 to 40° C. and left to stand to be separated into the upper organic layer containing crystals of the quinolone derivative represented by general formula (7) and the lower aqueous layer containing the aluminum halide represented by general formula (1), and then the aqueous layer is removed. An alcohol is added to the organic layer, followed by heating and washing such as heating under reflux, the addition of water, and further heating and washing such as heating under reflux. After cooling to 0 to 40° C., the crystals are removed by filtration. Moreover, the crystals can be washed with an aqueous alcohol solution as necessary.

The temperature during heating and washing is, for example, 40 to 100° C., and preferably 60 to 90° C. The time during heating and washing is, for example, 0.1 to 3 hours, and preferably 0.5 to 1.5 hours. The heating and washing may be performed once or a plurality of times.

The aqueous caustic solution to be used is an aqueous solution containing an alkali metal hydroxide, an alkaline earth metal hydroxide and the like. Specific examples thereof include an aqueous lithium hydroxide solution, an aqueous sodium hydroxide solution, an aqueous potassium hydroxide solution, an aqueous magnesium hydroxide solution, an aqueous calcium hydroxide solution and the like, preferably an aqueous sodium hydroxide solution or an aqueous potassium hydroxide solution. The concentration of the alkali metal hydroxide, the alkaline earth metal hydroxide and the like in the aqueous caustic solution is not particularly limited as long as the effects of the present invention are not impaired, and preferably 10% or more, and more preferably 20% to 50%. The amount of the aqueous caustic solution used is, not particularly limited as, long as the pH of the reaction solution during the post-treatment can be maintained at 11 or higher. The amount of the alkali metal hydroxide, the alkaline earth metal hydroxide and the like is 1.0- to 20.0-fold mol, and preferably 5.0- to 15.0-fold mol, relative to the anthranilic acid derivative represented by general formula (6).

The alcohol to be used is not particularly limited as long as the effects of the present invention are not impaired. In order to reduce the amount of alcohol used, the alcohol is preferably a higher alcohol equally high or higher than ethanol, more preferably a primary alcohol having 2 to 5 carbon atoms, and still more preferably ethanol from a economic viewpoint. The use of a higher alcohol equally high or higher than ethanol is preferable in that, in a reaction using aluminum chloride, when an alcohol is mixed in an aqueous caustic solution containing aluminum chloride, precipitation of aluminum crystals, which are slightly soluble except concentrated hydrochloric acid, is prevented. This is because aluminum crystals significantly lower purity by being mixed into a target product, and cause serious troubles in facilities by adhering to filtration facilities.

The amount of the alcohol used for heating and washing is preferably 100 to 1,000 mL, and more preferably 100 to 600 mL in total, relative to 1 mol of the anthranilic acid derivative represented by general formula (6) in order to prevent dissolution of a target product in the aqueous layer and the filtrate and to prevent a decrease in yield. The method of using the alcohol is more preferably a method of using 500 mL divided into two 250-mL portions.

As mentioned above, when a higher alcohol equally high or higher than ethanol is used as the alcohol, the amount of the alcohol used can be reduced as compared with the post-treatment step under acidic conditions.

Therefore, according to another embodiment of the production method of the present invention, there is provided a method for isolating a quinolone derivative represented by general formula (7) by the above filtration operation, and preferably a method in which ethanol is used under basic conditions so that industrially general production facilities such as a filter made of metal can be used.

The quinolone derivative produced and isolated by the production method of the present invention can be obtained as a higher purity isolated product by optionally purifying using a method by recrystallization.

These quinolone derivatives are useful as pharmaceutical and agricultural intermediates.

Moreover, the production method of the present invention is advantageous in that the quinolone derivative can be industrially produced in one-time production.

According to another embodiment of the present invention, there is provided a quinolone derivative represented by general formula (7) produced by the production method of the present invention.

The above embodiments of the quinolone derivative can be carried out according to the description of the production method of the present invention.

EXAMPLES

The present invention will be described more specifically below by way of Examples, but the technical scope of the present invention is not limited to these Examples. Unless otherwise specified, all percentages and ratios used in the present invention are by mass. Unless otherwise specified, units and measurement methods mentioned in the present specific are based on JIS standards.

In the following Examples and Reference Examples, the contents of the anthranilic acid derivative used and the quinolone derivative thus obtained were calculated by high-performance liquid chromatography using the respective standard products and internal standard substances. The standard product of each derivative is a substance obtained by purifying each derivative prepared by the method mentioned in WO 2010/007964 A by a method such as recrystallization or silica gel column chromatography.

Physical properties of isopropyl 2-amino-4-methyl-5-(4-(trifluoromethoxy)phenoxy)benzoate are shown below.

Melting point: 71-72° C.

$^1$H-NMR($CDCl_3$): 7.49 (1H, s), 7.12 (2H, J=9.3, 0.9) 6.85-6.80 (2H, m), 6.56 (1H, s), 5.63 (1H, broad), 5.18 (1H, hep, J=6.3), 2.09 (3H, s), 1.31 (6H, d, J=6.3)

Physical properties of a 2-ethyl-3,7-dimethyl-6-(4-(trifluoromethoxy)phenoxy)quinolone standard product are shown below.

Melting point: 281-283° C.

$^1$H-NMR (DMSO): 11.36 (1H, s), 7.44 (2H, s), 7.38 (2H, dd, J=9.3, J=0.9), 7.08-7.03 (2H, m), 2.69 (2H, q, J=7.5), 2.30 (3H, s), 1.97 (3H, s) 1.22 (3H, t, J=7.5)

Example 1

<Post-Treatment Under Basic Conditions>

[Chemical Formula 10]

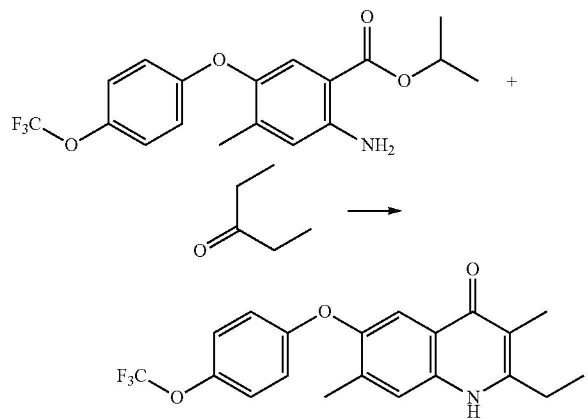

In a 2,000 mL four-necked flask, equipped with a stirrer, a thermometer and a reflux dehydrator, 54.00 g of aluminum chloride and 163.97 g of xylene were charged, followed by cooling to 10° C. Then, 34.82 g of 3-pentanone was added dropwise while keeping 20° C. or lower and, after stirring at 10 to 20° C. for 1 hour, a mixed solution of 48.68 g of tetrahydrothiophene-1,1-dioxide and 9132 g of xylene was added, and then a mixed solution of 105.54 g (content: 94.5%) of isopropyl 2-amino-4-methyl-5-(4-(trifluoromethoxy)phenoxy)benzoate and 209.04 g of xylene was added, followed by heating under reflux (135 to 138° C.) for 6 hours. During heating under reflux, a total of 270 mL of a reflux liquid was extracted and removed. Once cooling to room temperature, a separately mixed solution of 8.98 g of aluminum chloride, 47.84 g of xylene and 17.40 g of 3-pentanone was added in the reaction solution, followed by heating under reflux (136 to 140° C.) again for 8 hours. During heating under reflux, a total of 188 of a reflux liquid was extracted and removed. After completion of the reaction, the reaction solution was cooled to room temperature and then 433.38 g of an aqueous 25% sodium hydroxide solution and 67.5 mL of ethanol were added, followed by heating at 70 to 75° C. for 30 minutes, dropwise addition of 327.26 g of water and further heating at 70 to 75° C. for 30 minutes. After cooling to room temperature and standing, and separating into the aqueous layer which is the lower layer containing aluminum chloride and the organic layer which is the upper layer containing solid 2-ethyl-3,7-dimethyl-6-(4-(trifluoromethoxy)phenoxy)quinolone, the lower layer was separated and removed. To the organic layer, 67.5 of ethanol was added, followed by heating under reflux (84 to 85° C.) for 30 minutes, dropwise addition of 540 mL of water and further heating under reflux for 30 minutes. After cooling to room temperature, aging was performed at the same temperature for 30 minutes. Crystals were separated by filtration, washed with 216 mL of an aqueous 60% (v/v) ethanol solution and then dried to obtain 90.8 g (crude yield 89, content: 99.3%) of 2-ethyl-3,7-dimethyl-6-(4-(trifluoromethoxy)phenoxy)quinolone Melting point: 281-283° C.

$^1$H-NMR (DMSO): 11.36 (1H, s), 7.44 (2H, s), 7.38 (2H, dd, J=9.3, J=0.9), 7.08-7.03 (2H, m), 2.69 (2H q, J=7.5), 2.30 (3H, s), 1.97 (3H, s), 1.22 (3H, t, J=7.5)

Reference Example 1

<Post-Treatment Under Acidic Conditions>

In a 5,000 mL four-necked flask equipped with a stirrer, a thermometer and a reflux dehydrator, 149.99 g of aluminum chloride and 625 mL of xylene were charged, followed by cooling to 10° C. Then, 290.69 g of 3-pentanone was added dropwise while keeping 20° C. or lower, and then a mixed solution of 300 g (content: 92.3%) of isopropyl 2-amino-4-methyl-5-(4-(trifluoromethoxy)phenoxy)benzoate and 1,300 mL of xylene was added, followed by heating under reflux (133 to 137° C.) for 6 hours. During heating under reflux, a total of 440 mL of a reflux liquid was extracted and removed. Once cooling to 80° C., a separately mixed solution of 50.00 g of aluminum chloride, 250 mL of xylene and 96.90 g of 3-pentanone was added in the reaction solution, followed by heating under reflux (135 to 140° C.) again for 8 hours. During heating under reflux, a total amount of 100 mL of a reflux liquid was extracted and removed. After completion of the reaction, the reaction solution was cooled to 80° C. or lower and then 375 mL of an aqueous 5% hydrochloric acid solution was added dropwise to precipitate crystals, and 750 mL of methanol was added dropwise to completely dissolve the crystals. Moreover, 375 mL of water was added dropwise to precipitate crystals. After heating under reflux (70 to 74° C.) for 1 hour and cooling to 20° C., aging was performed at the same temperature for 1 hour, Crystals were separated by filtration, washed in turn with 750 mL of an aqueous 80% (v/v) methanol solution and 350 of water, and then dried to obtain 250.84 g (crude yield: 88.63%, content: 99.0%) of 2-ethyl-3,7-dimethyl-6-(4-(trifluoromethoxy)phenoxy)quinolone Melting point: 281-283° C.

$^1$H-NMR (DMSO): 11.36 (1H, s), 7.44 (2H, s), 7.38 (2H, dd, J=9.3, J=0.9), 7.08-7.03 (2H, m), 2.69 (2H q, J=7.5), 2.30 (3H, s), 1.97 (3H, s), 1.22 (3H, t, J=7.5)

Example 2

In a 500 mL four-necked flask equipped with a stirrer, a thermometer and a reflux dehydrator, 58.69 g (content; 94.6%) of isopropyl 2-amino-4-methyl-5-(4-(trifluoromethoxy)phenoxy)benzoate, 258.05 g of xylene, 19.18 g of 3-pentanone and 26.59 g of tetrahydrothiophene-1,1-dioxide were charged and stirred to give a uniform solution, and 30.04 g of aluminum chloride was added, followed by heating under reflux (135 to 138° C.) for 6 hours. During heating under reflux, a total of 150 mL of a reflux liquid was extracted and removed. Once cooling to room temperature, 25.49 g of xylene, 9.60 g of 3-pentanone and 5.06 g of aluminum chloride were added in this order in the reaction solution, followed by heating under reflux (136 to 140° C.) again for 6 hours. During heating under reflux, a total of 104 mL of a reflux liquid was extracted and removed. After completion of the reaction and cooling to room temperature, 242.51 g of an aqueous 25% sodium hydroxide solution and 37.5 mL of ethanol were added, followed by heating at 70 to 75° C. for 30 minutes, dropwise addition of 120 g of water and further heating at 70 to 75° C. for 30 minutes. After cooling to room temperature and standing, and separating into the aqueous layer which is the lower layer containing aluminum chloride and the organic layer which is the upper layer containing solid 2-ethyl-3,7-dimethyl-6-(4-(trifluoromethoxy)phenoxy)quinolone, the lower layer was separated and removed. To the organic layer, 37.5 mL of ethanol was added, followed by heating at 70 to 80° C. for 30 minutes, dropwise addition of 300 mL of water and further heating at 70 to 80° C. for 30 minutes. After cooling to room temperature, aging was performed at the same temperature for 30 minutes. Crystals were separated by filtration, washed with 120 of an aqueous 60% (v/v) ethanol solution and then dried to obtain 45.87 g (crude yield: 80.86%, content: 99.0%) of 2-ethyl-3,7-dimethyl-6-(4-(trifluoromethoxy)phenoxy)quinolone Melting point: 281-283° C.

$^1$H-NMR (DMSO): 11.36 (1H, s), 7.44 (2H, s), 7.38 (2H, dd, J=9.3, J=0.9), 7.08-7.03 (2H, m), 2.69 (2H, q, J=7.5), 2.30 (3H, s), 1.97 (3H, s), 1.22 (3H, t, J=7.5)

The invention claimed is:

1. A method for producing a quinolone derivative represented by formula (7):

(7)

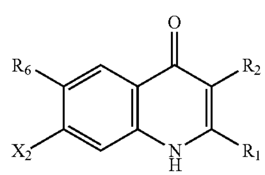

wherein $R_1$, $R_2$, $R_6$, and $X_2$ are as defined below, the method comprising, in the presence of an aluminum halide represented by formula (1):

$AlZ_3$ (1)

wherein Z represents a halogen atom, reacting a ketone represented by formula (2):

(2)

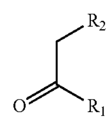

wherein $R_1$ and $R_2$ each independently represent:

an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{3-8}$ cyclic aliphatic hydrocarbon group, an optionally substituted aromatic hydrocarbon group, or an optionally substituted heterocyclic group, alternatively, $R_1$ and $R_2$ are combined together to represent a group —$(CH_2)_p$— (in which p represents 2 to 6), wherein each of the substituents in the linear or branched $C_{1-4}$ alkyl group, the linear or branched $C_{2-4}$ alkenyl group and the linear or branched $C_{2-4}$ alkynyl group is at least one group selected from the group consisting of a halogen atom and a $C_{1-4}$ alkoxy group optionally substituted with a halogen atom, the substituent in the $C_{3-8}$ cyclic aliphatic hydrocarbon group is at least one group selected from the group consisting of a linear or branched $C_{1-4}$ alkyl group, a halogen atom, and a $C_{1-4}$ alkoxy group optionally substituted with a halogen atom, the substituent in the aromatic hydrocarbon group is at least one group selected from the group consisting of a halogen atom, a linear or branched $C_{1-4}$ alkyl group optionally substituted with a halogen atom, a linear or branched $C_{1-4}$ alkoxy group optionally substituted with a halogen atom, and a phenoxy group which is optionally substituted with a linear or branched $C_{1-4}$ alkoxy group optionally substituted with a halogen atom, and the substituent in the heterocyclic group is at least one group selected from the group consisting of a halogen atom, a linear or branched $C_{1-4}$ alkyl group optionally substituted with a halogen atom, and a linear or branched $C_{1-4}$ alkoxy group optionally substituted with a halogen atom, with an anthranilic acid derivative represented by formula (6):

(6)

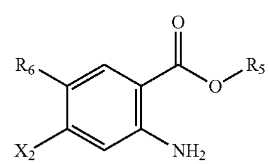

wherein $R_5$ represents:

an optionally substituted linear or branched $C_{1-4}$ alkyl group, or an optionally substituted $C_{3-8}$ cyclic aliphatic hydrocarbon group, $R_6$ represents a hydrogen atom, a halogen atom, or —B—$R_7$, wherein, B represents:

an oxygen atom, a sulfur atom, $N(R_8)$, $N(R_8)$—CO, or CO—$N(R_8)$, $R_7$ and $R_8$ each independently represent:

a hydrogen atom, an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted $C_{3-8}$ cyclic aliphatic hydrocarbon group, an optionally substituted aromatic hydrocarbon group, or an optionally substituted heterocyclic group, wherein each of the substituents in the linear or branched $C_{1-4}$ alkyl group, the linear or branched $C_{2-4}$ alkenyl group, and the linear or branched $C_{2-4}$ alkynyl group is at least one group selected from the group consisting of a halogen atom and a $C_{1-4}$ alkoxy group optionally substituted with a halogen atom, the substituent in the $C_{3-8}$ cyclic aliphatic hydrocarbon group is at least one group selected from the group consisting of a linear or branched $C_{1-4}$ alkyl group, a halogen atom, and a $C_{1-4}$ alkoxy group optionally substituted with a halogen atom, and each of the substituents in the aromatic hydrocarbon group and the heterocyclic group is at least one group selected from the group consisting of:

a halogen atom, a linear or branched $C_{1-4}$ alkyl group optionally substituted with a halogen atom, a linear or branched $C_{1-4}$ alkyl group which is optionally substituted with a $C_{1-4}$ alkoxy group optionally substituted with a halogen atom, a linear or branched $C_{2-4}$ alkenyl group optionally substituted with a halogen atom, a linear or branched $C_{2-4}$ alkenyl group which is optionally substituted with a $C_{1-4}$ alkoxy group optionally substituted with a halogen atom, a linear or branched $C_{2-4}$ alkynyl group optionally substituted with a halogen atom, a linear or branched $C_{2-4}$ alkynyl group which is optionally substituted with a $C_{1-4}$ alkoxy group optionally substituted with a halogen atom, a linear or branched $C_{1-4}$ alkoxy group optionally substituted with a halogen atom, a linear or branched $C_{1-4}$ alkoxy group which is optionally substituted with a $C_{1-4}$ alkoxy group optionally substituted with a halogen atom, a linear or branched $C_{2-4}$ alkenyloxy group optionally substituted with a halogen atom, a linear or branched $C_{2-4}$ alkenyloxy group which is optionally substituted with a $C_{1-4}$ alkoxy group optionally substituted with a halogen atom, a linear or branched $C_{2-4}$ alkynyloxy group optionally substituted with a halogen atom, a linear or branched $C_{2-4}$ alkynyloxy group which is optionally substituted with a $C_{1-4}$ alkoxy group optionally substituted with a halogen atom, and a phenoxy group which is optionally substituted with a linear or branched $C_{1-4}$ alkoxy group optionally substituted with a halogen atom, and $X_2$ represents:

a hydrogen atom, a halogen atom, an optionally substituted linear or branched $C_{1-4}$ alkyl group, or an optionally substituted linear or branched $C_{1-4}$ alkoxy group, in which each of the substituents in the linear or branched $C_{1-4}$ alkyl group, and the linear or branched $C_{1-4}$ alkoxy group is at least one group selected from the group consisting of a halogen atom and a $C_{1-4}$ alkoxy group optionally substituted with a halogen atom;

and removing the aluminum halide under basic conditions.

2. The method according to claim 1, comprising a step of mixing the aluminum halide represented by formula (1) in advance with the ketone represented by formula (2).

3. The method according to claim 1, comprising a step of further adding a sulfide represented by formula (4):

$$R_3—S(=O)_l—R_4 \qquad (4)$$

in which $R_3$ and $R_4$ each independently represent an optionally substituted linear or branched $C_{1-4}$ alkyl group, or $R_3$ and $R_4$ are combined together to represent a group —$(CH_2)_q$— (q is 3 to 7), and 1 represents 1 or 2, to a mixture of the aluminum halide represented by formula (1) and the ketone represented by formula (2).

4. The method according to claim 3, wherein

Z represents a halogen atom, $R_1$ and $R_2$ each independently represent:

an optionally substituted linear or branched $C_{1-4}$ alkyl group, an optionally substituted linear or branched $C_{2-4}$ alkenyl group, or an optionally substituted linear or branched $C_{2-4}$ alkynyl group, in which each of the substituents in the linear or branched $C_{1-4}$ alkyl group, the linear or branched $C_{2-4}$ alkenyl group, and the linear or branched $C_{2-4}$ alkynyl group is at least one group selected from the group consisting of a halogen atom and a $C_{1-4}$ alkoxy group optionally substituted with a halogen atom, $R_3$ and $R_4$ are combined together to represent a group —$(CH_2)_q$— (q is 3 to 7), and 1 represents 1 or 2, $R_5$ represents a linear or branched $C_{1-4}$ alkyl group, or a $C_{3-8}$ cyclic aliphatic hydrocarbon group, $R_6$ represents a hydrogen atom, a halogen atom, or —B—$R_7$, wherein B represents an oxygen atom, a sulfur atom, $N(R_8)$, $N(R_8)$—CO, or CO—$N(R_8)$, $R_7$ and $R_8$ each independently represent a halogen atom, or an aromatic hydrocarbon group which is optionally substituted with a linear or branched $C_{1-4}$ alkoxy group optionally substituted with a halogen atom, and $X_2$ represents a hydrogen atom, a halogen atom, a linear or branched $C_{1-4}$ alkyl group optionally substituted with a halogen atom, or a linear or branched $C_{1-4}$ alkoxy group optionally substituted with a halogen atom.

5. The method according to claim 1, wherein the aluminum halide represented by formula (1) is aluminum chloride.

6. The method according to claim 1, wherein the ketone represented by formula (2) is 3-pentanone.

7. The method according to claim 1, wherein the anthranilic acid derivative represented by formula (6) represents the following formula (8):

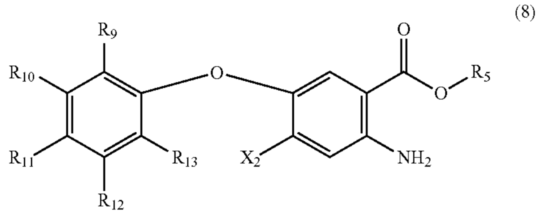

wherein $R_5$ and $X_2$ are as defined above, $R_9$, $R_{10}$, $R_{11}$, $R_{12}$, and $R_{13}$ each independently represent:

a hydrogen atom, a halogen atom, an optionally substituted linear or branched $C_{1-4}$ alkyl group, an optionally substituted linear or branched $C_{2-4}$ alkenyl group, an optionally substituted linear or branched $C_{2-4}$ alkynyl group, an optionally substituted linear or branched $C_{1-4}$ alkoxy group, an optionally substituted linear or branched $C_{2-4}$ alkenyloxy group, or, an optionally substituted linear or branched $C_{2-4}$ alkynyloxy group, in which each of the substituents in $R_9$, $R_{10}$, $R_{11}$, $R_{12}$, and $R_{13}$ is at least one group selected from the group consisting of a halogen atom and a $C_{1-4}$ alkoxy group optionally substituted with a halogen atom.

8. The method according to claim 3, wherein the sulfide represented by formula (4) is tetrahydrothiophene-1,1-dioxide.

9. The method according to claim 1, wherein the removal of the aluminum halide under basic conditions is performed by filtration under basic conditions using an aqueous caustic solution and an alcohol.

10. The method according to claim 1, wherein the quinolone derivative represented by formula (7) represents the following formula (9):

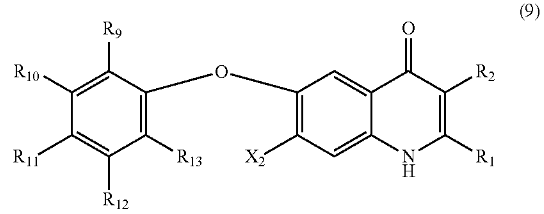

wherein $R_1$, $R_2$, $R_9$, $R_{10}$, $R_{11}$, $R_{12}$, $R_{13}$, and $X_2$ are as defined above.

11. The method according to claim 1, wherein the quinolone derivative represented by formula (7) is 2-ethyl-3,7-dimethyl-6-(4-(trifluoromethoxy)phenoxy)quinolin-4(1H)-one.

* * * * *